US012806362B2

(12) United States Patent
Heesch et al.

(10) Patent No.: US 12,806,362 B2
(45) Date of Patent: Nov. 24, 2026

(54) SUPPLY ARRANGEMENT AND PROCESS FOR SAFELY SUPPLYING A MEDICAL DEVICE WITH A GAS MIXTURE

(71) Applicant: Drägerwerk AG & Co. KGaA, Lübeck (DE)

(72) Inventors: Ralf Heesch, Lübeck (DE); Sven Pasdzior, Lübeck (DE); Klaus Radomski, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 1071 days.

(21) Appl. No.: 17/869,922

(22) Filed: Jul. 21, 2022

(65) Prior Publication Data

US 2023/0041741 A1 Feb. 9, 2023

(30) Foreign Application Priority Data

Jul. 22, 2021 (DE) ......................... 102021119000.2

(51) Int. Cl.
*A61M 16/10* (2006.01)
*A61M 16/00* (2006.01)
(Continued)

(52) U.S. Cl.
CPC ...... *A61M 16/104* (2013.01); *A61M 16/0003* (2014.02); *A61M 16/024* (2017.08);
(Continued)

(58) Field of Classification Search
None
See application file for complete search history.

(56) References Cited

U.S. PATENT DOCUMENTS 3,515,155 A * 6/1970 Haffner ................. A61M 16/12 137/7
5,558,083 A * 9/1996 Bathe .................. A61M 16/204 128/203.14

(Continued)

FOREIGN PATENT DOCUMENTS

DE 4112119 A1 10/1992
DE 202011102318 U1 11/2011

(Continued)

OTHER PUBLICATIONS

"EP_0566488_B1.pdf" is a translation with paragraph numbers. (Year: 2025).*

*Primary Examiner* — Timothy A Stanis
*Assistant Examiner* — Thomas Z Chang
(74) *Attorney, Agent, or Firm* — McGlew and Tuttle, P.C.

(57) ABSTRACT

A supply arrangement (100) and a process supply a medical device (50, 90) with a supply gas mixture. The supply gas mixture includes a carrier gas and an anesthetic and is generated by an anesthetic dispenser (3). A carrier gas mixing unit (9) generates the carrier gas from at least two carrier gas components. A carrier gas switch having a regular outlet and a discharge outlet selectively directs carrier gas components to the carrier gas mixing unit or to a discharge line (35). A gas mixture switch (6), having a regular outlet (41) and a discharge outlet (42) selectively directs the supply gas mixture to the medical device or to the discharge line (35). An anesthetic concentration sensor (5.1, 5.2) measures a concentration of anesthetic in the generated gas mixture. A control unit (2) controls the gas mixture switch based on measured concentration within or outside a predefined range.

16 Claims, 6 Drawing Sheets

(51) Int. Cl.
*A61M 16/12* (2006.01)
*A61M 16/14* (2006.01)
*A61M 16/18* (2006.01)

(52) U.S. Cl.
CPC ............ *A61M 16/12* (2013.01); *A61M 16/14* (2013.01); *A61M 16/18* (2013.01); *A61M 2016/1035* (2013.01)

(56) References Cited

U.S. PATENT DOCUMENTS

| | | | | |
|---|---|---|---|---|
| 9,283,347 | B2 | 3/2016 | Heesch | |
| 2004/0168686 | A1* | 9/2004 | Krebs | A61M 16/009 128/200.24 |
| 2006/0207593 | A1* | 9/2006 | Dittmann | A61M 16/104 128/203.14 |
| 2008/0264417 | A1* | 10/2008 | Manigel | A61M 16/0063 128/205.12 |
| 2010/0095961 | A1* | 4/2010 | Tornesel | A61M 16/0051 128/205.24 |
| 2019/0099581 | A1* | 4/2019 | Kuzelka | A61M 16/024 |
| 2020/0353200 | A1* | 11/2020 | McCormick | A61M 16/22 |
| 2022/0211965 | A1* | 7/2022 | Orth | A61M 16/0833 |

FOREIGN PATENT DOCUMENTS

| | | | | |
|---|---|---|---|---|
| DE | 102016001383 | A1 | 8/2017 | |
| EP | 0566488 | B1 * | 9/1996 | B01F 23/12 |
| EP | 2170447 | B1 | 7/2017 | |
| WO | 2007006348 | A1 | 1/2007 | |

* cited by examiner

SUPPLY ARRANGEMENT AND PROCESS FOR SAFELY SUPPLYING A MEDICAL DEVICE WITH A GAS MIXTURE

CROSS REFERENCE TO RELATED APPLICATIONS

This application claims the benefit of priority under 35 U.S.C. § 119 of German Application 10 2021 119 000.2, filed Jul. 22, 2021, the entire contents of which are incorporated herein by reference.

TECHNICAL FIELD

The invention relates to a supply arrangement and a process which are capable of supplying a medical device with a supply gas mixture. In particular, the medical device is an anesthesia device which at least temporarily anesthetizes or sedates a patient. The supply gas mixture is a mixture of a carrier gas and anesthetic (one or more anesthetic agents). The carrier gas comprises at least two carrier gas components. At least one carrier gas component is or comprises oxygen.

TECHNICAL BACKGROUND

In many applications, this supply gas mixture must or should meet at least one predetermined characteristic. For example, the concentration of the anesthetic or even oxygen in the supply gas mixture must be within a predetermined range so as not to endanger the patient while the patient is connected to the anesthesia machine. Or, the humidity or temperature or pressure of the supply gas mixture must be within a predetermined range.

DE 41 12 119 A1 describes an arrangement which is capable of supplying an anesthetic device with a supply gas mixture comprising an anesthetic and fresh gas. An anesthetic evaporator with an evaporation chamber 1 and a metering device 2 is capable of generating the supply gas mixture. A change-over valve 6 receives an evaporation chamber flow 5 from the evaporation chamber 1 and directs the evaporation chamber flow 5 to an outlet 16 or to an outlet 15, depending on the control. The outlet 16 leads to an anesthetic gas connection 8 for the anesthetic device. Outlet 15 leads to an anesthetic gas delivery line 17. After a start-up of the anesthetic vaporizer, the evaporation chamber flow 5 is first directed to anesthetic gas delivery line 17 to prevent overdosing of a patient and then to the anesthetic device.

SUMMARY

The invention is based on the object of providing a supply arrangement and process for supplying a medical device with a supply gas mixture, the supply gas mixture comprising anesthetic (one or more anesthetic agent) and a carrier gas having at least two carrier gas components, and wherein the supply arrangement and process are intended to ensure, with a relatively high degree of reliability, that the supply gas mixture delivered to the medical device actually satisfies a predetermined characteristic.

The task is solved by a supply arrangement and by a process according to the invention. Advantageous embodiments are indicated in the subclaims. Advantageous embodiments of the supply arrangement according to the invention are, as far as useful, also advantageous embodiments of the process according to the invention and vice versa.

The supply arrangement according to the invention and the process according to the invention are capable of supplying a medical device with a supply gas mixture. In particular, the medical device is an anesthesia device capable of supplying a patient with a supply gas mixture comprising anesthetic. The medical device may also be a patient-side coupling unit, such as a breathing mask or a tube, wherein the patient-side coupling unit is connected or connectable to a patient.

The supply gas mixture supplied to the medical device comprises a carrier gas and anesthetic (one or more anesthetic agents). The carrier gas is composed of at least two carrier gas components, optionally at least three carrier gas components. At least one carrier gas component is or comprises oxygen. The supply gas mixture may comprise anesthetic with at least two anesthetic agents.

The supply arrangement according to the invention comprises an anesthetic dispenser and a carrier gas supply line. The carrier gas supply line is capable of supplying the carrier gas to the anesthetic dispenser. The anesthetic dispenser is configured to feed the anesthetic into the supplied carrier gas or to mix the anesthetic with the carrier gas in some other way, thereby generating the supply gas mixture.

The supply arrangement further comprises a controllable pneumatic gas mixture switch (controllable gas diverter valve). A “pneumatic switch” is understood to mean a component having an inlet and at least two outlets, the switch directing a fluid flowing through the inlet to one of the at least two outlets depending on its position.

The gas mixture switch of the supply arrangement comprises an inlet and two outlets, namely a regular outlet and a discharge outlet. A gas mixture connection line connects the anesthetic dispenser to the inlet of the gas mixture switch. The gas mixture switch is thus located downstream of the anesthetic dispenser. The supply gas mixture which the anesthetic dispenser has generated and which comprises a carrier gas and anesthetic can flow through this gas mixture connection line from the anesthetic dispenser to the gas mixture switch.

A gas mixture supply line leads from the regular outlet of the gas mixture switch to the medical device or to a line which in turn leads to the medical device. The supply gas mixture can flow through this gas mixture supply line to the medical device.

In one embodiment, a discharge line connects the discharge outlet of the gas mixture switch to a gas receptacle. This gas receptacle (gas sink) is spatially separated from the medical device and is part of a stationary infrastructure or a treatment facility for medical gases, for example. In another embodiment, the discharge line leads from the discharge outlet into the environment of the supply arrangement, for example out of a building into the open air.

The supply arrangement further comprises a carrier gas switch arrangement comprising of at least one pneumatic carrier gas switch having an inlet, a regular outlet, and at least one discharge outlet. The regular outlet is connected to a component of a carrier gas mixing unit or to the anesthetic dispenser. In one embodiment, the or at least one carrier gas switch is disposed between two components of the carrier gas mixing unit. The term “between” refers to a direction of flow of fluid through the carrier gas mixing unit.

The respective discharge outlet of the or each carrier gas switch is connected to a discharge line arrangement. The discharge outlet of the gas mixture switch and the discharge outlet of the or a carrier gas switch can be connected to the same discharge line or to two different discharge lines. Also, the further discharge line leads to the environment or to a treatment facility. In one embodiment, the regular outlet of the or at least one carrier gas switch is connected to an inlet of the anesthetic dispenser.

Each switch, that is, both the gas mixture switch and the or each carrier gas switch, can be operated in either a regular position or a discharge position. In the regular position, a fluid connection is established between the inlet and the regular outlet of that switch, and the switch directs a fluid from the inlet to the regular outlet. In the discharge position, a fluid connection is established between the inlet and the discharge outlet of this switch, and the switch directs a fluid from the inlet to the discharge outlet. Preferably, each switch can be selectively operated in the regular position or the discharge position independently of the current position of any other switch, and can be transitioned from one position to the other position independently of any other switch.

When the gas mixture switch is in the regular position, the gas mixture switch directs the supply gas mixture, which flows through the gas mixture connection line to the inlet, to the regular outlet. The supply gas mixture continues to flow to the medical device, and the medical device can supply a patient with the supply gas mixture. When the gas mixture switch is in the discharge position, the gas mixture switch directs the supply gas mixture from the inlet to the discharge outlet. The supply gas mixture flows into the discharge line.

According to the invention, the supply arrangement further comprises a carrier gas mixing unit. This carrier gas mixing unit is capable of mixing the carrier gas using at least two carrier gas components. At least one carrier gas component is or comprises oxygen. These carrier gas components are, for example, breathing air, pure oxygen, nitrous oxide (N2O), xenon or HeliOx.

The carrier gas supply line leads from the carrier gas mixing unit to the anesthetic dispenser. The carrier gas therefore flows from the carrier gas mixing unit through the carrier gas supply line to the anesthetic dispenser. The anesthetic dispenser feeds the anesthetic into the carrier gas, wherein this carrier gas has been composed of at least two carrier gas components by the carrier gas mixing unit. In another embodiment, the carrier gas mixing unit feeds at least one component of the carrier gas into a stream of breathing air or oxygen or other gas at a first feed point so as to form a mixture having at least two carrier gas components, and the anesthetic dispenser feeds the anesthetic into the stream at a second feed point, with a gap occurring between the two feed points.

The or each carrier gas switch in the regular position directs a gas or gas mixture flowing through the inlet of the carrier gas switch to its regular outlet. In particular, the gas is a carrier gas component or a mixture of at least two carrier gas components, but may also be the final carrier gas. The regular outlet is connected to a component of the carrier gas mixing unit or to the anesthetic dispenser, so that the gas or gas mixture flows to that component or to the anesthetic dispenser. The or each carrier gas switch in the discharge position directs the gas or gas mixture from the inlet to the discharge outlet. From there, it flows into the discharge line arrangement.

The process according to the invention is carried out using such a supply arrangement. The process comprises the following steps:

- The carrier gas mixing unit generates the carrier gas. For this purpose, the carrier gas mixing unit uses the at least two carrier gas components.
- The anesthetic dispenser generates the supply gas mixture. For this purpose, the anesthetic dispenser uses the anesthetic as well as the carrier gas which the carrier gas mixing unit has generated.
- The or each carrier gas switch directs a gas or gas mixture flowing through the inlet of the carrier gas switch to either the regular outlet or the discharge outlet of the carrier gas switch. This gas or gas mixture is in particular a carrier gas component or a mixture of at least two carrier gas components. The outlet to which the carrier gas switch directs the gas or gas mixture depends on whether the carrier gas switch is currently in the regular position or in the discharge position.
- The gas mixture switch directs the supply gas mixture to the regular outlet or to the discharge outlet of the gas mixture switch. This supply gas mixture was generated by the anesthetic dispenser. The outlet to which the gas mixture switch directs the supply gas mixture depends on whether the gas mixture switch is in the regular position or in the discharge position.

If the gas mixture switch directs the supply gas mixture to its discharge outlet, the supply gas mixture is prevented from reaching the medical device and thus the patient. This effect is produced particularly when the patient could be harmed by the supply gas mixture. Thanks to the discharge line, it is not necessary for the supply arrangement to discharge the supply gas mixture directly into the environment, which is undesirable in many cases. This is because the supply gas mixture includes anesthetic. Rather, it is possible for the discharge line to direct the supply gas mixture to a treatment facility or a disposal facility.

According to the invention, the or at least one carrier gas switch is capable of conducting a gas or gas mixture to a component of the carrier gas mixing unit, to the anesthetic dispenser or to the discharge line arrangement, depending on the position and arrangement. In many cases, this feature allows a carrier gas to be provided even if a carrier gas component is not available at all, or is not available at the sufficient flow rate or pressure or temperature, or is not currently needed. The or a carrier gas switch then directs this carrier gas component into the discharge line, and the carrier gas mixing unit generates the carrier gas using the or at least one, preferably any other carrier gas component that is sufficiently available.

In addition, the use of a carrier gas switch allows the supply arrangement to be used first for a first medical treatment and then for a second medical treatment. A carrier gas component is needed for the first treatment, but not for the second treatment. Therefore, before the second treatment, this carrier gas component must be removed from the anesthetic dispenser. The carrier gas switch in the appropriate position directs the carrier gas component that is not required for the second treatment to the discharge outlet. This carrier gas component is then no longer directed to the anesthetic dispenser, which makes it possible to remove any remaining quantity of this carrier gas component from the anesthetic dispenser, for example at the end of the first treatment.

The effects just described can be achieved solely by the respective position of each switch. It is not necessary to temporarily disconnect a connection between two components of the supply arrangement and to re-establish it later. This feature makes it easier in many cases to operate the supply arrangement according to the invention automatically and/or remotely monitored.

According to the invention, each switch can be operated either in a regular position or in a discharge position. Depending on its position, the switch passes a fluid from its inlet to its regular outlet or to its discharge outlet. Various embodiments are possible as to how a particular position of a switch (valve) can be established.

In a first embodiment, the supply arrangement additionally comprises at least one actuation unit for a switch, the or each actuation unit being assigned to at least one switch in each case. With the aid of the actuation unit, a user can manually transfer the associated switch from one position to the other position. Preferably, the actuation unit comprises a manually operable actuation element and a mechanical or pneumatic transfer element. In many cases, this embodiment enables a switch to be adjusted without requiring electrical power. It is possible that the same actuation unit is assigned to at least two different switches. These switches can then generally only be adjusted together.

In a second embodiment, the supply arrangement additionally comprises an input unit and at least one actuator that is assigned to a switch. With the aid of this input unit, a user can select a switch of the supply arrangement and specify the position in which the selected switch is to be located. The actuator for the selected switch transfers this switch to the specified position. In one implementation form, the input unit displays textually and/or graphically which switch the supply arrangement comprises, and preferably the respective current position of each switch. With the aid of a touch screen or other input element, the user can select a switch and then specify a desired position for the switch.

In a third embodiment, the supply arrangement additionally comprises a signal-processing control unit. The control unit is capable of receiving and automatically processing signals, in particular signals from sensors and/or from an input unit. Furthermore, the control unit is able to automatically control at least one switch. By actuating the switch, the control unit causes the switch to be in the regular position or in the discharge position. If required, a controlled actuator transfers the switch from one position to the other. It is possible for the control unit to control at least one switch automatically, i.e. without user input, and to change its position.

At least two of these three embodiments can be combined. It is possible that the position of the same switch can be changed in at least two of the following ways:

- A user actuates the actuating element.
- A user makes an input on the input unit and the actuator changes the position of the switch.
- The control unit automatically controls the switch, i.e. without any user input, and thus changes the position of the switch.

It is also possible that a first switch can be changed with the actuating element, a second switch can be changed by an input at the input unit, and/or a third switch can be changed by a control by the control unit. It is also possible that the same switch can be adjusted in at least two different ways. This provides redundancy.

In a preferred embodiment, the supply arrangement comprises the aforementioned control unit and a state sensor arrangement comprising at least one state sensor, preferably several state sensors. The optional control unit receives in each case a signal from the or at least one state sensor and is able to control the gas mixture switch and/or at least one carrier gas switch depending on the respective signal of at least one state sensor.

The state sensor arrangement measures an indicator for at least one of the following:

- for a state of the generated supply gas mixture, in particular for the concentration of the anesthetic or also of the carrier gas or a carrier gas component in the supply gas mixture or also for the temperature or humidity or pressure or volume flow of the supply gas mixture,
- for a state of the carrier gas, in particular for the concentration of the or a component of the carrier gas or for the temperature or humidity or pressure or volume flow of the carrier gas,
- for a state of the anesthetic dispenser, in particular for a volume flow of anesthetic which the anesthetic dispenser achieves, and/or for the concentration of the anesthetic in the supply gas mixture, and/or whether the anesthetic dispenser is intact and switched on or not,
- for a state of the carrier gas mixing unit, in particular for the achieved volume flow of the carrier gas, or
- for a condition of another component of the supply arrangement.

The volume flow of a fluid is understood to be the volume of fluid that flows through a fluid guide unit per unit of time.

According to the preferred embodiment, the optional control unit controls the gas mixture switch or the carrier gas switch as follows:

- When the or each state measured by a state sensor is within a predetermined allowable range (set range), respectively, the gas mixture switch directs the supply gas mixture from its inlet to its regular outlet. Or, the or a carrier gas switch directs a gas or gas mixture from its inlet to its regular outlet.
- Otherwise, i.e. if at least one state is outside the respective specified regular range, the gas mixture switch directs the supply gas mixture from the inlet to the discharge outlet. Or the or a carrier gas switch directs a gas or gas mixture from the inlet to the discharge outlet.
- Optionally, a permissible regular range is specified for a combination of several states. If the combination of the measured states is within the range, the gas mixture switch directs the supply gas mixture to the regular outlet, otherwise to the discharge outlet. The carrier gas switch directs the gas or gas mixture to the regular outlet if the measured combination is within the range, and otherwise to the discharge outlet.

This embodiment reduces the risk of a supply gas mixture with an unacceptable property (characteristic) flowing from the regular outlet of the gas mixture switch to the medical device during operation. Only when the measured condition or each measured condition, or optionally the combination of conditions, is within the allowable range can the supply gas mixture reach the patient. This reduces the risk of the patient being endangered by an inappropriate supply gas mixture. It also reduces the risk of an unsuitable carrier gas reaching the anesthetic dispenser.

It is also possible that a signal is output from a state sensor in a manner that can be perceived by a human and a user operates an actuation unit for a switch.

According to a preferred embodiment, the supply arrangement according to the invention comprises at least one anesthetic concentration sensor, optionally several anesthetic concentration sensors. The anesthetic concentration sensor is a special case of a state sensor and is capable of measuring an indicator for the actual concentration of the anesthetic in the generated supply gas mixture at a respective measuring point. The or each measurement point is located in the anesthetic dispenser or downstream of the anesthetic dispenser, i.e., between the anesthetic dispenser and the medical device. In the case of multiple anesthetic concentration sensors, a distance preferably occurs between each two measurement points. At least one measurement point is particularly preferably located downstream of the other measurement point. The measured concentration is, for example, the concentration itself or at least one volume flow rate of a component of the supply gas mixture or also a measured feed rate at which the anesthetic dispenser feeds the anesthetic into the carrier gas, or a pressure in a mixing tank of the anesthetic dispenser.

According to the embodiment with the anesthetic concentration sensor, the optional control unit controls the gas mixture switch depending on a signal from the anesthetic concentration sensor, optionally a signal from each of a plurality of anesthetic concentration sensors, as follows:

- If the measured concentration of the anesthetic or one anesthetic agent or each anesthetic agent in the supply gas mixture is within a specified required concentration range, the gas mixture switch directs the supply gas mixture to the regular outlet.
- Otherwise, i.e. if the measured concentration is outside the required concentration range, the gas mixture switch directs the supply gas mixture to the discharge outlet.

If there are several measuring points, the gas mixture switch preferably directs the supply gas mixture to the regular outlet if a correct concentration is measured at least at the measuring point furthest downstream.

According to the embodiment with the anesthetic concentration sensor, the concentration of the anesthetic in the supply gas mixture is measured at at least one measuring point in the anesthetic dispenser or between the anesthetic dispenser and the medical device, whereby the anesthetic dispenser provides this supply gas mixture. This supply gas mixture is only passed on to the medical device if the concentration of the anesthetic is within the predetermined concentration range. Otherwise, the supply gas mixture is directed to the discharge line and on to the gas receptacle. This feature ensures that only a supply gas mixture with a correct concentration of anesthetic reaches the medical device, and thus the patient connected to the medical device, and not one with an incorrect concentration. This embodiment facilitates maintaining the concentration of the anesthetic in the supply gas mixture within the required concentration range. If the anesthetic concentration becomes too small or becomes too large, the supply gas mixture is directed into the discharge line until the anesthetic concentration has dropped again and is back within the required concentration range.

If the concentration of the anesthetic is incorrect, i.e., too high or too low, the supply gas mixture is instead directed through the discharge line to the gas receptacle or into the environment. On the one hand, this feature prevents with a high degree of certainty that a supply gas mixture with an incorrect concentration reaches the patient. On the other hand, the feature significantly reduces the risk of the anesthetic leaking into the environment of the supply arrangement or medical device. This is usually undesirable, especially if the medical device is in an enclosed space, because the anesthetic could endanger people in the vicinity of the medical device.

The carrier gas mixing unit generates the carrier gas as a gas mixture of at least two carrier gas components. As a rule, each component of the carrier gas should be present in the generated carrier gas at a concentration that lies within a required concentration range specified for this carrier gas component. Alternatively, the required concentration range specifies the concentration at which this carrier gas component is to occur in the supply gas mixture. Preferably, the supply arrangement comprises at least one carrier gas component concentration sensor. The or each carrier gas component concentration sensor measures an indicator for the concentration of a respective carrier gas component in the generated carrier gas or in the generated supply gas mixture. For example, the measure is directly the concentration or a volume flow of a carrier gas component. This measured concentration of the carrier gas component may be within or outside the concentration range specified for that carrier gas component.

In one embodiment, the optional control unit is able to automatically control the gas mixture switch or the or a carrier gas switch depending on a signal from the or at least one carrier gas component concentration sensor, optionally on a signal from a corresponding sensor per carrier gas component. If the concentration of at least one component of the carrier gas is outside a permissible required concentration range, the controlled gas mixture switch directs the supply gas mixture to the discharge outlet and thus into the discharge line. Or the actuated carrier gas switch directs a gas or gas mixture flowing through this carrier gas switch to the discharge outlet. This arrangement is preferably used in particular when the concentration of oxygen or breathing air in the carrier gas or supply gas mixture is too low.

In one application, this embodiment reduces or even eliminates the risk of the patient receiving a supply gas mixture with insufficient oxygen. Also, in some cases, it reduces the risk of the anesthetic dispenser being supplied with an unsuitable or poorly suitable carrier gas. In addition, this embodiment makes it easier to keep the concentration of the carrier gas component within the specified required concentration range.

In one embodiment, the control unit controls the carrier gas switch such that the carrier gas switch directs a carrier gas that reaches the inlet of the carrier gas switch to an outlet as follows:

- If the measured concentration of the carrier gas component is within the carrier gas concentration range specified for this carrier gas component, the carrier gas switch directs the carrier gas to the regular outlet, i.e., to an outlet connected to the carrier gas supply line or to a line leading to the carrier gas supply line. The carrier gas is then directed to the anesthetic dispenser.
- If the control unit receives signals from multiple carrier gas component concentration sensors, the carrier gas switch directs the carrier gas to the regular outlet when the respective measured concentration of each carrier gas component is within the carrier gas concentration range specified for that carrier gas component.

According to the invention, the carrier gas mixing unit is able to generate the carrier gas using at least two carrier gas components. In one embodiment, the supply arrangement comprises a carrier gas component supply line for each carrier gas component, which supplies the carrier gas mixing unit with this carrier gas component. The or a carrier gas switch is assigned to at least one carrier gas component. The inlet of this carrier gas switch is connected to the carrier gas component supply line. The regular outlet is connected to a component of the carrier gas mixing unit, the discharge outlet to the discharge line.

In one further variation of this embodiment, the supply arrangement for at least one carrier gas component comprises a carrier gas component volume flow sensor. This sensor is capable of measuring an indicator for the actual volume flow of the carrier gas component through the associated carrier gas component supply line, i.e., it is capable of measuring the amount of carrier gas component flowing through the carrier gas component supply line per unit time. The control unit is able to decide whether the measured volume flow is within a specified target volume flow range or not.

The control unit is able to control the assigned carrier gas switch as follows:

If the measured actual volume flow of the carrier gas component through the carrier gas component supply line is within the specified target volume flow range, the controlled carrier gas switch directs the carrier gas component to the regular outlet of the carrier gas switch. The regular outlet is connected to the carrier gas mixing unit.

If, on the other hand, the measured actual volume flow is outside the target volume flow range, the controlled carrier gas switch directs the carrier gas component to the discharge outlet. This discharge outlet is connected to the discharge line.

In many cases, this form of implementation makes it possible to provide a carrier gas even though at least one component of the carrier gas cannot be provided at all or cannot be provided with the required volume flow. This form of implementation is particularly advantageous if oxygen and/or breathing air can be provided with sufficient volume flow, but another carrier gas component cannot.

Two possible embodiments of how the carrier gas mixing unit and subsequently the anesthetic dispenser generates a supply gas mixture comprising the carrier gas components and the anesthetic from the carrier gas components and the anesthetic are a serial embodiment and a cascaded embodiment. These two embodiments are described below.

In the serial embodiment, two carrier gas components are first mixed to form an intermediate gas mixture, and then one further carrier gas component and/or the or in each case an anesthetic are added successively to the intermediate gas mixture produced so far. The mixing unit components used are thus connected in series.

In the cascaded (staged) embodiment, two intermediate gas mixtures are generated in a first stage from at least two components in each case. In a subsequent second stage, optionally in several second stages, the supply gas mixture comprising the carrier gas and the anesthetic is generated from these intermediate gas mixtures.

In both embodiments, the carrier gas is preferably composed of at least three carrier gas components, for example, breathing air, pure oxygen, and N2O.

In both embodiments, the carrier gas mixing unit comprises a first mixer and a second mixer. The first mixer generates an intermediate gas mixture using the first and second carrier gas components. The second mixer generates the carrier gas using the intermediate gas mixture and the third carrier gas component.

According to the invention, the supply arrangement comprises at least one carrier gas switch. In one embodiment, the or one carrier gas switch is arranged between the first mixer and the second mixer. Both mixers comprise an inlet and an outlet, respectively. More specifically, the inlet of the carrier gas switch is connected to an outlet of the first mixer. The intermediate gas mixture generated by the first mixer flows to the carrier gas switch. The regular outlet of the carrier gas switch is connected to an inlet of the second mixer so that the intermediate gas mixture can continue to flow to the second mixer when the carrier gas switch is in the regular position. The discharge outlet of the carrier gas switch is connected to the discharge line. In the discharge position, the carrier gas switch therefore directs the intermediate gas mixture into the discharge line.

This embodiment makes it possible to still provide a carrier gas even if the first and/or the second carrier gas component is not available at all or not available in sufficient quantity. The carrier gas is then generated using the or each sufficiently available carrier gas component.

Preferably, the control unit is able to control the carrier gas switch between the two mixers of the carrier gas mixing unit. In one embodiment, the supply arrangement comprises a carrier gas component concentration sensor. This carrier gas component concentration sensor is capable of measuring an indicator for the concentration of the first and/or the second carrier gas component in the intermediate gas mixture or in the carrier gas. The control unit controls the carrier gas switch depending on a signal from the carrier gas component concentration sensor. If the concentration of the first and/or the second carrier gas component is within a predefined required concentration range, the carrier gas switch directs the intermediate gas mixture to the second mixer, otherwise to the discharge line arrangement.

The embodiment just described allows the carrier gas to be generated using the third carrier gas component, while the intermediate gas mixture is fed into the discharge line with the carrier gas switch in an appropriate position. A further embodiment of the supply arrangement allows the reverse procedure, namely to generate the carrier gas using the first and second carrier gas components without using the third carrier gas component. It is also possible to switch the carrier gas switch several times, thereby reducing the concentration of the third carrier gas component in the carrier gas.

According to a further embodiment, the carrier gas mixing unit comprises a first mixer and a second mixer, wherein a mixer connection line connects the outlet of the first mixer to an inlet of the second mixer. The supply arrangement includes a mixer bypass line. This mixer bypass line is connected to the mixer connection line, bypasses the second mixer and is connected to the carrier gas supply line. Further, the supply arrangement includes a pneumatic mixer bypass switch having an inlet, a regular outlet, and a bypass outlet. The inlet of the mixer bypass switch is connected to an outlet of the first mixer. When the mixer bypass switch is in a regular position, the mixer bypass switch routes an intermediate gas mixture from the first mixer to the second mixer. The bypass outlet of the mixer bypass switch is connected to the mixer bypass line. Thus, when it is in the bypass position, the mixer bypass switch directs the intermediate gas mixture into the mixer bypass line, and the intermediate gas mixture flows past the second mixer into the carrier gas supply line.

Depending on the position of the mixer bypass switch, the second mixer is involved or not involved in generating the carrier gas.

In a variation of this further embodiment, the supply arrangement comprises a carrier gas component concentration sensor. This carrier gas component concentration sensor is capable of measuring an indicator for the actual concentration of the third carrier gas component in the carrier gas or the supply gas mixture. The control unit is able to control the mixer bypass switch depending on a signal from the carrier gas component concentration sensor. If the actual concentration of the third carrier gas component is within a predetermined required concentration range, the mixer bypass switch directs the intermediate gas mixture to the regular outlet, and the intermediate gas mixture flows to the second mixer so that the second mixer can add the third carrier gas component. Otherwise, the mixer bypass switch directs the intermediate gas mixture to the bypass outlet, and the intermediate gas mixture flows through the mixer bypass line around the second mixer to the carrier gas supply line.

The further embodiment is particularly advantageous if the intermediate gas mixture comprises sufficient oxygen to supply a patient and the supply gas mixture can therefore also be generated using the intermediate gas mixture without necessarily requiring the third carrier gas component. Thus, medical treatment of the patient can continue even if the third carrier gas component is not available at all or is not available in sufficient quantity.

According to the invention, the anesthetic dispenser generates a supply gas mixture from a carrier gas and anesthetic. The medical device is supplied with the supply gas mixture by means of the gas mixture supply line. The embodiment described below makes it possible to supply the patient optionally with the supply gas mixture or only with the carrier gas. It is possible to supply the patient at times with the supply gas mixture and at times only with the carrier gas. The configuration described below is particularly advantageous if it is detected that the anesthetic dispenser is not working at all or is not working correctly. It is particularly advantageous when the anesthetic dispenser adds a relatively large amount of the anesthetic to the carrier gas. In many cases, it is also possible to repair the anesthetic dispenser without having to remove another component of the supply arrangement. The embodiment described below also allows the supply arrangement to be used initially for a first treatment in which a supply gas mixture containing anesthetic is supplied to a patient, and subsequently for a second treatment in which a supply gas mixture without anesthetic is supplied to that or another patient, for example the carrier gas.

According to the embodiment, the supply arrangement comprises a carrier gas bypass line. This carrier gas bypass line bypasses the anesthetic dispenser and opens into the gas mixture supply line. Preferably, the carrier gas bypass line opens into the gas mixture supply line downstream of the gas mixture switch, so that the carrier gas bypass line also bypasses the gas mixture switch. It is also possible that the carrier gas bypass line opens into the gas mixture supply line upstream of the gas mixture switch.

According to this embodiment, the supply arrangement further comprises a pneumatic carrier gas bypass switch having an inlet, a regular outlet, and a bypass outlet. The inlet is connected to the carrier gas mixing unit so that carrier gas can flow to the carrier gas bypass switch. The regular outlet is connected to the carrier gas supply line. The bypass outlet of the carrier gas bypass switch is connected to the carrier gas bypass line. If the carrier gas bypass line opens into the gas mixture supply line upstream of the gas mixture switch, the bypass outlet of the carrier gas bypass switch is also connected to the gas mixture switch.

When the carrier gas bypass switch is in a regular position, it directs the carrier gas into the regular outlet and thus into the carrier gas supply line so that the carrier gas can flow to the anesthetic dispenser. If the carrier gas bypass switch is in a bypass position, it directs the carrier gas through the bypass outlet into the carrier gas bypass line and thus into the gas mixture supply line. Thus, depending on the position of the carrier gas bypass switch, the carrier gas flows through the regular outlet and the carrier gas supply line into the anesthetic dispenser or through the bypass outlet around the anesthetic dispenser into the gas mixture supply line. Thus, in the second case, the carrier gas is not enriched with an anesthetic.

In one implementation, the control unit can control the carrier gas bypass switch. It is also possible for the carrier gas bypass switch to be adjusted manually by means of an actuating element.

In one further variation of this embodiment, the supply arrangement comprises an anesthetic concentration sensor. This anesthetic concentration sensor is configured to measure an indicator for the actual concentration of the anesthetic, or at least one anesthetic agent, in the supply gas mixture. The control unit is adapted to control the carrier gas bypass switch in response to a signal from the anesthetic concentration sensor. The control has the following effect: If the actual concentration of the anesthetic in the supply gas mixture is within a predetermined required concentration range, the carrier gas bypass switch directs the carrier gas to the regular outlet so that the carrier gas continues to flow to the anesthetic dispenser. Otherwise, the carrier gas bypass switch directs the carrier gas to the bypass outlet so that the carrier gas flows around the anesthetic dispenser to the gas mixture supply line.

In an embodiment further comprising the carrier gas bypass switch and the carrier gas bypass line, the supply arrangement further comprises at least one buffer storage (buffer reservoir). The or a buffer storage is in fluid communication with the gas mixture supply line, thus is arranged downstream of the anesthetic dispenser and downstream of the gas mixture switch. As long as the gas mixture switch directs the supply gas mixture into the gas mixture supply line, it is possible for the buffer storage to be filled with the supply gas mixture. If the gas mixture switch directs the supply gas mixture into the discharge line or a technical defect has occurred, the patient can still be supplied with the supply gas mixture from the buffer storage for a period of time. How long this period is depends on the volume of the supply gas mixture that the buffer storage has taken up and stored. In one embodiment, the volume of this buffer storage can be changed, for example because the buffer storage comprises an expandable bag. Particularly preferably, this buffer storage is or comprises a hand-held respiratory bag.

According to the invention, the carrier gas mixing unit generates the carrier gas using at least two carrier gas components. Generally, the supply arrangement comprises a carrier gas component supply line for at least one carrier gas component, preferably a carrier gas component supply line for each carrier gas component. The or each carrier gas component supply line may be connected to a stationary supply connection or to a reservoir for the carrier gas component, for example to a compressed air cylinder. Preferably, the or a carrier gas switch is disposed between the carrier gas component supply line for a carrier gas component and the carrier gas mixing unit. The carrier gas component supply line is connected to the inlet of this carrier gas switch. The regular outlet of the carrier gas switch is connected to a carrier gas mixing unit component, and the discharge outlet is connected to the discharge line arrangement comprising at least one discharge line. In the regular position, the carrier gas switch directs the carrier gas component from the carrier gas component supply line to the component of the carrier gas mixing unit. In the discharge position, it directs the carrier gas component from the carrier gas component supply line to the discharge line arrangement.

In one embodiment, the control unit automatically controls this carrier gas switch depending on a signal from a carrier gas component concentration sensor. The carrier gas component concentration sensor is able to measure the actual concentration of the carrier gas component in the carrier gas or in the supply gas mixture. The actuated carrier gas switch directs the carrier gas component to the carrier gas mixing unit if the measured concentration of the carrier gas component is within a predetermined required concentration range, and to the discharge line arrangement otherwise. This embodiment makes it easier to keep the concentration of the carrier gas component in the carrier gas or in the supply gas mixture within the required concentration range.

In a further embodiment, the control unit controls the carrier gas component switch based on a signal from a carrier gas component volume flow sensor. This carrier gas component volume flow sensor is capable of measuring an indicator for the actual volume flow of the carrier gas component through the associated carrier gas component supply line. The control of the carrier gas component switch does the following: If the actual volume flow is within a predetermined target volume flow range, the carrier gas switch directs the carrier gas component to the regular outlet so that the carrier gas component flows to the carrier gas mixing unit. Otherwise, the carrier gas switch directs the carrier gas component to the discharge outlet so that the carrier gas component flows into the discharge line.

The embodiment with the carrier gas component concentration sensor and the embodiment with the carrier gas component volume flow sensor can be combined.

In one embodiment, the supply arrangement can optionally be operated in a supply mode or in an initialization mode. In the supply mode, the anesthetic dispenser is activated and can feed the anesthetic into the carrier gas. In initialization mode, the anesthetic dispenser is deactivated. In the initialization mode, the gas mixture switch is controlled to connect the inlet to the discharge outlet. This prevents a carrier gas without anesthetic from reaching the medical device in the initialization mode.

Preferably, in the initialization mode, the carrier gas is passed through the supply arrangement without an anesthetic being added to the carrier gas. For example, in the initialization mode, an anesthetic is removed from a mixing chamber of the anesthetic dispenser by the carrier gas flowing through the mixing chamber and taking the anesthetic with it. Anesthetic may still be present in the mixing chamber due to a previous use. Or, the lines of the supply arrangement are checked for leaks, with the respective pressure being measured at various measuring points. Or, a supply connection, which provides the carrier gas or a component of the carrier gas, or the carrier gas mixing unit are checked for functionality. Even in the initialization mode, it is ensured that neither anesthetic nor carrier gas escapes into the environment. Rather, even in the initialization mode, the supply gas mixture is fed into the discharge line.

In one embodiment, the supply arrangement is operated in the initialization mode before use and in supply mode during use. It is also possible that the supply arrangement is switched from supply mode to the initialization mode and back to supply mode during use. This double switchover is performed, for example, if a fault is detected in the anesthetic dispenser and it is therefore necessary, in particular, to switch the anesthetic dispenser off, switch it on, and calibrate it again. It is also possible to switch the supply arrangement to the initialization mode after operation in supply mode.

The invention further relates to an anesthesia system comprising a patient-side coupling unit and a supply arrangement according to the invention. The patient-side coupling unit is connected or at least temporarily connectable to the patient and preferably comprises a breathing mask and/or a tube. The patient-side coupling unit is capable of supplying a supply gas mixture to the patient. The gas mixture supply line connects the regular outlet of the gas mixture switch to the patient-side coupling unit. This allows the gas mixture generated by the supply arrangement to be delivered to the patient-side coupling unit. Preferred embodiments of the supply arrangement according to the invention are also preferred embodiments of the anesthesia system.

In one embodiment, the patient's own breathing activity causes the patient to be supplied with the supply gas mixture which is provided by the supply arrangement and which is conducted, in particular conveyed, to the coupling unit on the patient's side. The patient draws in the supply gas mixture himself. The patient's own respiratory activity is brought about by the patient's respiratory musculature, in particular by the patient's spontaneous breathing and/or by a device stimulating the respiratory musculature externally.

In another embodiment, the anesthesia system further comprises a ventilator. Preferably, the ventilator is capable of performing a sequence of ventilation strokes. The gas mixture supply line extends from the regular outlet of the gas mixture switch to the ventilator. The ventilator is capable of delivering a quantity of the gas mixture to the patient-side coupling unit in each ventilation stroke.

In the following, the invention is described by means of an embodiment example. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
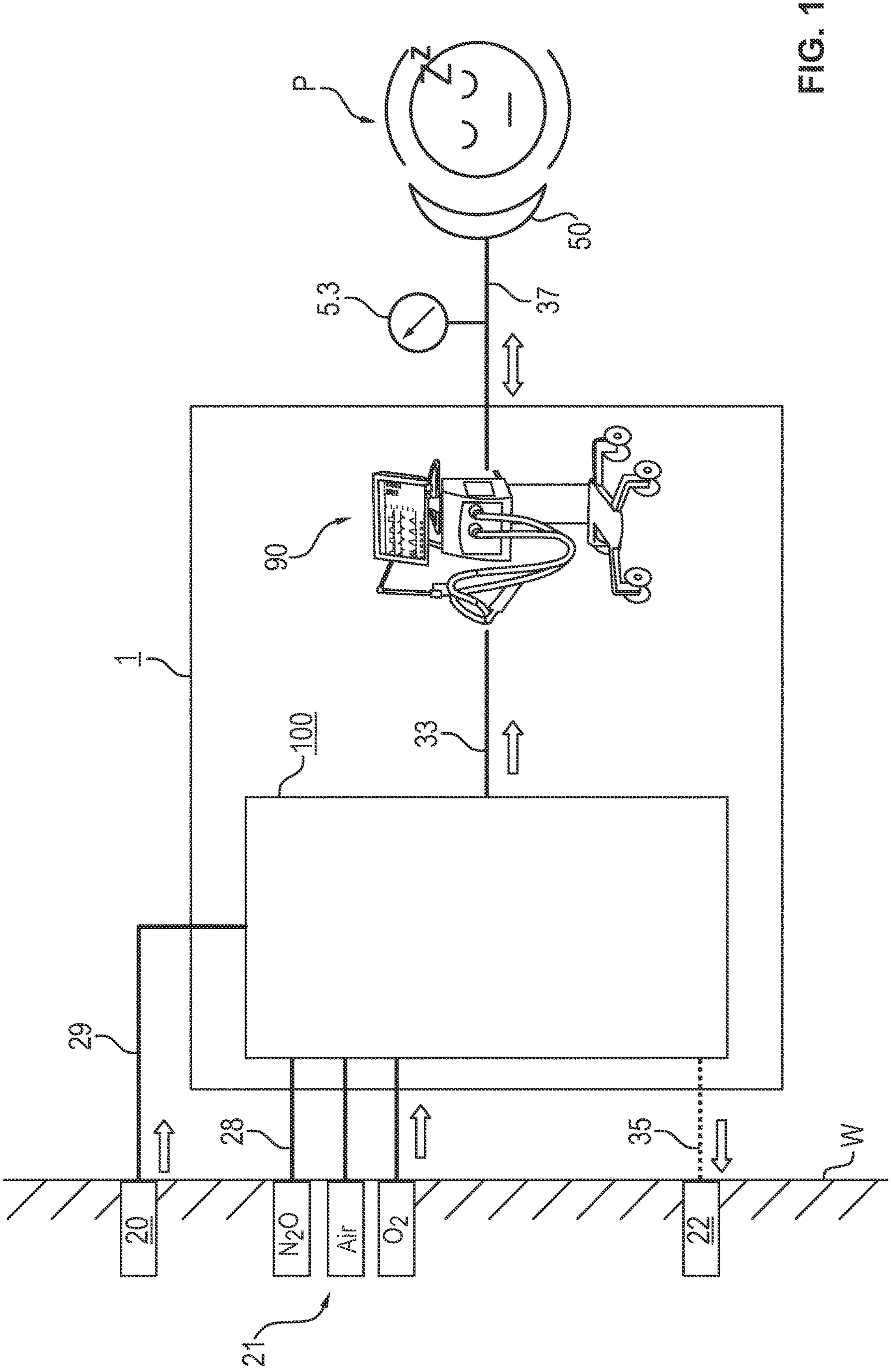
FIG. 1 is a schematic view showing the integration of a supply arrangement according to the invention into a system which artificially ventilates and anesthetizes a patient.

In the embodiment example, the invention is used in an anesthesia system 1, with the aid of which a patient P is artificially ventilated and anesthetized. FIG. 1 schematically shows the patient, the system 1 and its supply of fluids.

The patient P is connected to a schematically shown patient-side coupling unit 50 during artificial respiration, for example with a breathing mask on the face or a tube or catheter in the body. The anesthesia system 1 is connected to the patient-side coupling unit 50 by a line arrangement 37 comprising a plurality of parallel lines (lumens). Thus, a closed ventilation circuit is established between the patient P and the anesthesia system 1.

The anesthesia system 1 includes a ventilator 90 that performs a sequence of ventilation strokes. During each ventilation stroke, a quantity of a supply gas mixture flows from the ventilator 90 through a lumen of the line arrangement 37 to the patient-side coupling unit 50 and further to the patient P. The supply gas mixture comprises a carrier gas with oxygen and anesthetic. An optional anesthetic concentration sensor 5.3 measures the concentration of the anesthetic in the supply gas mixture flowing through the line arrangement 37 to the patient-side coupling unit 50. Exhaled air flows through another lumen of the line arrangement 37 from the patient P back to the anesthesia system 1. The anesthesia system 1 maintains the closed ventilation circuit between the ventilator 90 and the patient P. The anesthesia system 1 is configured to provide a closed ventilation circuit between the patient P and the ventilator 90. Preferably, the ventilator 90 removes carbon dioxide from the exhaled air. It is possible that patient P is fully anesthetized and is ventilated solely by the artificial ventilation. It is also possible that the artificial ventilation supports the patient P's own respiratory activity.

In an alternative embodiment not shown, the ventilator 90 is omitted. Also in this alternative embodiment, the patient P is supplied with a supply gas mixture comprising a carrier gas with oxygen and anesthetic, and also in this alternative embodiment, the patient P is at least temporarily connected to the patient-side coupling unit 50. The patient P takes in the supply gas mixture by means of the patient P's own respiratory activity, i.e., by means of his own respiratory muscles. For example, patient P performs sufficiently strong spontaneous breathing. Or patient P's own respiratory musculature is stimulated externally, for example by electrical pulses or in a magnetic field. It is possible that the externally stimulated respiratory activity supports the patient P's spontaneous breathing.

The following description refers to the embodiment according to FIG. 1 and can be transferred to the alternative embodiment. The carrier gas in the embodiment example consists of three components, namely the three gases breathing air, oxygen and nitrous oxide (N2O). It is also possible that the carrier gas comprises fewer and/or more or other components. In any embodiment, the carrier gas comprises oxygen as one component, for example pure oxygen or breathing air with oxygen. It is also possible that the anesthetic is added directly to a stream of breathing air. In this case, this stream of breathing air acts as the carrier gas to which the anesthetic is added. The stream of breathing air can circulate in the closed ventilation circuit. Preferably, the ventilator 90 maintains this ventilation circuit.

The supply arrangement 100 of the embodiment according to the invention is part of the anesthesia system 1 and supplies the ventilator 90 or directly the coupling unit 50 on the patient side with this gas mixture. A gas mixture supply line 33 leads from the supply arrangement 100 to the ventilator 90 or directly to the patient-side coupling unit 50.

A stationary supply port 21 in a wall W provides the three gaseous components breathing air, oxygen and nitrous oxide (N2O) for the carrier gas. These three components are supplied to the supply arrangement 100 via the three lines 28. It is possible for the supply port 21 to provide at least one additional or different component, or even fewer than three components. Also in this case, the carrier gas is generated from the provided carrier gas components and comprises oxygen. It is also possible that the supply arrangement 100 is supplied with the carrier gas components from mobile storage containers, for example metal bottles.

A supply port 20 in wall W provides compressed air or oxygen or other pressurized gas. The pressurized gas is directed to the supply arrangement 100 through a line (conduit) 29. The use of this positive pressure is described further below.

A discharge configuration comprising at least one discharge line 35 leads from the supply arrangement 100 to a gas receptacle (gas sink) 22 in the wall W. The discharge line 35 is capable of leading a gas mixture from the supply arrangement 100 to the gas receptacle 22. This gas mixture may contain anesthetic and in particular may be the supply gas mixture.

The discharge line 35 and the gas receptacle 22 prevent a gas mixture containing an anesthetic from entering the environment of the anesthesia system 1, where it could harm people's health. Preferably, the gas receptacle 22 further prevents this gas mixture from entering a room and/or another device in the hospital via the inpatient infrastructure system of a hospital.

In one embodiment, the gas receptacle 22 is connected to a suction system, such as a pump, wherein said suction system draws a gas mixture through the discharge line 35 to the gas receptacle 22. In another embodiment, the gas mixture is delivered to the gas receptacle 22 by an overpressure. In a third embodiment, a hose downstream of the gas receptacle 22 directs the gas mixture to a filter arrangement that filters out anesthetic from the gas mixture. In a further embodiment, a gas line downstream of the gas receptacle 22 directs the gas mixture to another processing system or disposal system. It is also possible that the gas receptacle 22 discharges the gas mixture into the open air.

In the embodiment described below, the carrier gas is generated from three components: oxygen (O2), breathing air, and nitrous oxide (N2O), and gaseous anesthetic is fed into this carrier gas. The ventilator 90 is supplied with a supply gas mixture of the carrier gas and the anesthetic, and the supply gas mixture is fed into the ventilation circuit. It is also possible that the carrier gas is fed into the ventilation circuit at a first feed point and the anesthetic is fed into the ventilation circuit at a spatially spaced second feed point. It is also possible that at times no separate carrier gas is used and only the gaseous anesthetic is fed into the ventilation circuit.

Figure 2:
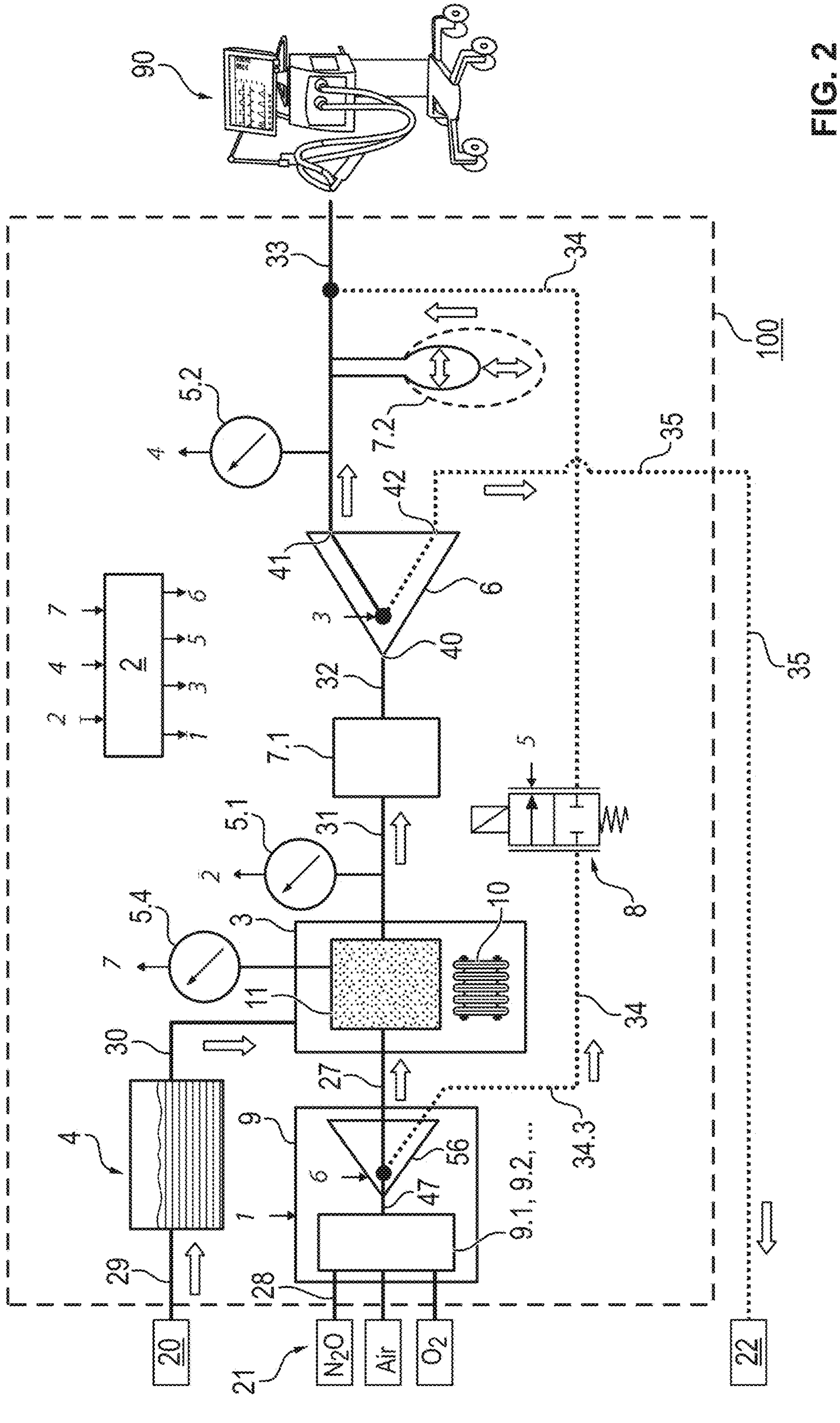
FIG. 2 is a schematic view showing the structure of the supply arrangement of FIG. 1 according to the invention.

FIG. 2 schematically shows the structure of the supply arrangement 100 according to the invention. The following components of the supply arrangement 100 are shown:

- an anesthetic dispenser 3, which generates the supply gas mixture from the carrier gas and the anesthetic and comprises a mixing chamber 11, in which the anesthetic is added to the carrier gas,
- a volume flow sensor 5.4 that measures an indicator for the volume flow of anesthetic into the mixing chamber 11, for example the saturated vapor flow of anesthetic,
- a heater 10 for the mixing chamber 11 of the anesthetic dispenser 3,
- an anesthetic tank 4 for liquid anesthetic,
- the line 29 through which the pressurized gas flows from the supply port 20 to the anesthetic tank 4,
- a front anesthetic concentration sensor 5.1 and a rear anesthetic concentration sensor 5.2, each measuring an indicator for the concentration of the anesthetic in the supply gas mixture generated by the anesthetic dispenser 3, wherein the designations "front" and "rear" refer to the direction of flow of the supply gas mixture to the ventilator 90, a carrier gas mixing unit 9, which generates the carrier gas from the three gases breathing air, oxygen and nitrous oxide and comprises a plurality of mixers 9.1, 9.2, . . . , the three lines 28 through which the three carrier gas components breathing air, oxygen and nitrous oxide flow from the supply connections 21 to the carrier gas mixing unit 9, a pneumatic gas mixture switch (diverter) 6 comprising a switch, the gas mixture switch 6 comprising an inlet 40, a regular outlet 41, and a discharge outlet 42, the discharge line 35 leading from the discharge outlet 42 of the gas mixture switch 6 to the gas receptacle 22, optionally a front buffer storage (front buffer reservoir) 7.1 and a rear buffer storage (rear buffer reservoir) 7.2 between the anesthetic dispenser 3 and the ventilator 90, wherein each buffer storage 7.1, 7.2 can temporarily store the supply gas mixture, i.e. can receive a certain quantity of the gas mixture and later release it again, the gas mixture supply line 33 leading from the regular outlet 41 of the gas mixture switch 6 to the ventilator 90, and a signal processing control unit 2.

The three anesthetic concentration sensors 5.1, 5.2 and 5.3 and the volume flow sensor 5.4 are arranged at different measuring points and measure at least one variable at the respective measuring point which correlates with the anesthetic concentration in the gas mixture, for example directly the concentration, a volume flow, a cycle rate of an injection system for an anesthetic or also several of these variables. Optionally, a pressure sensor not shown measures the pressure over time in the mixing chamber 11. The volume flow of anesthetic can be approximately derived from the measured pressure in the mixing chamber 11, the flow of carrier gas into the mixing chamber 11, and the known volume of the mixing chamber 11. This embodiment creates redundancy because the volume flow of anesthetic is calculated in two different ways.

The three anesthetic concentration sensors 5.1, 5.2 and 5.3 optionally apply at least two different measuring principles. The control unit 2 is able to determine the concentration of the anesthetic at the respective measuring point from the measured values of the three anesthetic concentration sensors 5.1, 5.2 and 5.3 and the volume flow sensor 5.4. This concentration can vary not only over time, but also from measuring point to measuring point.

In the figures, these three as well as optionally further concentration sensors are arranged at different measuring points. Preferably, the anesthesia system 1 comprises a central concentration measuring unit, which is connected to each of the different measuring points via a fluid guide unit, as well as a selection arrangement, which ensures that the concentration measuring unit is pneumatically connected to exactly one measuring point at any time, optionally to no measuring point at all during a pause in operation. The gas mixture is guided from the respective measuring point through the fluid guide unit to the concentration measuring unit and preferably through another lumen of the same fluid guide unit back to the measuring point. This embodiment makes it possible to measure the respective concentration at different measuring points and still require only one central concentration measuring unit. The selection arrangement comprises, for example, one controllable switching valve per measuring point and thus per fluid guide unit.

The gaseous anesthetic is added to the carrier gas in the mixing chamber 11. The anesthetic dispenser 3 can add anesthetic to the carrier gas, in particular by vaporization or evaporation or by injection. For example, an injection valve not shown injects liquid anesthetic into the mixing chamber 11, and there the liquid anesthetic is heated and thereby becomes gaseous. Or the liquid anesthetic is vaporized in the mixing chamber 11, for example with the aid of the heater 10, and thereby becomes gaseous.

The optional front buffer storage 7.1 is located between the mixing chamber 11 and the gas mixture switch 6, and the optional rear buffer storage 7.2 is located between the regular outlet 41 of the gas mixture switch 6 and the ventilator 90. In the embodiment, the front buffer storage 7.1 and the gas mixture switch 6 are located outside the ventilator 90. The rear buffer storage 7.2 may be located inside or outside the ventilator 90. In the embodiment shown in FIG. 2, the rear buffer storage 7.2 is located outside the ventilator 90 and is in fluid communication with the gas mixture supply line 33.

In one embodiment, the capacity of the connecting line 31 is such that the connecting line 31 itself acts as a buffer storage and a separate front buffer storage 7.1 is not used. Accordingly, in one embodiment, the capacity of the gas mixture supply line 33 is such that the gas mixture supply line 33 itself acts as a buffer storage and a separate rear buffer storage 7.2 is not used. In this embodiment, the volume of the line 31 or 33 is preferably variable.

A rear carrier gas supply line 27 guides the carrier gas from the carrier gas mixing unit 9 to the mixing chamber 11. A line 30 guides liquid anesthetic from the anesthetic tank 4 to the anesthetic dispenser 3. A connecting line 31 guides the generated gas mixture from the mixing chamber 11 of the anesthetic dispenser 3 to the front buffer storage 7.1. A connecting line 32 leads from the front buffer storage 7.1 to the inlet 40 of the gas mixture switch 6. The gas mixture supply line 33 leads from the regular outlet 41 of the gas mixture switch 6 to the ventilator 90.

A bypass line 34 for oxygen, breathing air and/or nitrous oxide leads from the carrier gas mixing unit 9 to the gas mixture supply line 33. This bypass line 34 bypasses the anesthetic dispenser 3, the two buffer storages 7.1 and 7.2 and the gas mixture switch 6 and opens into the gas mixture supply line 33 downstream of the regular outlet 41 of the gas mixture switch 6. A bypass switch 56 with an inlet, a regular outlet and a bypass outlet is part of the mixing unit 9 and is capable of selectively directing oxygen, breathing air and/or nitrous oxide from the carrier gas mixing unit 9 into the carrier gas supply line 27 or into the bypass line 34. A front carrier gas supply line 47 leads from the mixers 9.1, 9.2, . . . to the inlet of the bypass switch 56. An optional controllable proportional valve 8 in the bypass line 34 can block the bypass line 34 or change the flow rate of gas through the bypass line 34.

The front anesthetic concentration sensor 5.1 measures an indicator for the concentration of the anesthetic in the supply gas mixture flowing through the connection line 31 to the front buffer storage 7.1. The rear concentration sensor 5.2 measures the concentration of anesthetic in the supply gas mixture flowing through the gas mixture supply line 33 to the ventilator 90.

The supply arrangement 100 is operable in a supply mode. In the supply mode, the supply arrangement provides the supply gas mixture of the carrier gas with oxygen and anesthetic. Before the supply arrangement 100 is operated in the supply mode during anesthetization of the patient P, it is operated in an initialization mode. In particular, operation in the initialization mode has the following objectives:

Anesthetic which may be present from a previous use in the anesthetic dispenser 3 or in a line of the supply arrangement 100 is removed. Such anesthetic still present from a previous use could lead to incorrect dosing of the anesthetic in the current use.

The functionality of the supply arrangement 100 without the anesthetic dispenser 3 and the functioning of the supply connections 21 are checked.

Lines of the supply arrangement 100 are checked for leaks.

In addition, the initialization mode allows a first medical treatment to be performed using an anesthetic and a subsequent second medical treatment to be performed using the same supply arrangement 100 not using an anesthetic. Therefore, anesthetic must be removed from the supply arrangement 100 prior to commencing the second treatment.

The carrier gas mixing unit 9 also generates the carrier gas in the initialization mode. However, the anesthetic dispenser 3 is deactivated and therefore does not feed any anesthetic into the carrier gas. The carrier gas flows through the supply arrangement 100 to the gas mixture switch 6. Any anesthetic present is carried along by the carrier gas and thus removed from the anesthetic dispenser 3. While the supply arrangement 100 is operating in the initialization mode, the gas mixture switch 6 directs the carrier gas from the inlet 40 to the discharge outlet 42. The carrier gas enters the discharge line 35 and does not reach the ventilator 90 or the patient-side coupling unit 50.

Optionally, the respective pressure in different lines of the supply arrangement 100 is measured. If the pressure measured in a downstream measuring point is significantly lower than a pressure measured in an upstream measuring point, an indication of leakage is found. If the pressure at each measuring point is too low, a supply port 21 may not be supplying enough gas.

A user or also a higher-level signal-processing control unit specifies a setpoint concentration of the anesthetic in the supply gas mixture, whereby the ventilator 90 and thus the patient P are to be supplied with this supply gas mixture. This setpoint concentration can be variable over time. The control unit 2 receives measured values from the anesthetic concentration sensors 5.1, 5.2 and 5.3 and from the volume flow sensor 5.4. The anesthetic concentration sensors 5.1, 5.2 and 5.3 directly measure, for example, the concentration or the volume flow or the clock rate of an injection system of the anesthetic dispenser 3. It is possible that the anesthetic concentration sensors 5.1, 5.2 and 5.3 and the volume flow sensor 5.4 apply at least two different measuring principles in total. Depending on measured values, the control unit 2 determines the temporal course of the actual concentration of the anesthetic in the supply gas mixture, which flows through the connection line 31 or the gas mixture supply line 33 or the line arrangement 37, at the respective measuring point.

Preferably, the control unit 2 performs a closed-loop control or an open-loop control with the aim of ensuring that the specified time profile of the setpoint concentration matches the time profile of the measured actual concentration of the anesthetic in the supply gas mixture. The control unit 2 controls two valves, not shown, in the carrier gas supply lines 47 or 27 and 30, and optionally an injection valve in the mixing chamber 11, in order to change the actual concentration of the anesthetic in the gas mixture generated in the mixing chamber 11 in the event of a control deviation. For this control, the control unit 2 uses the measured values from the front anesthetic concentration sensor 5.1, which is located upstream of the front buffer storage 7.1. In many cases, the control interventions effected by the control unit 2 lead to a rapid reduction of the control deviation. The generated gas mixture flows through the front buffer storage 7.1. In many cases, this results in the actual concentration of the anesthetic in the gas mixture supply line 33 differing less from the target concentration than the actual concentration in the connection line 31. In addition, the front buffer storage 7.1 reduces the time fluctuations of the control deviation.

The concentration of the anesthetic in the supply gas mixture flowing through the gas mixture supply line 33 to the ventilator 90 must be within a predetermined target range. The concentration must not be less than the lower bound of this target range in order for the patient P to remain reliably anesthetized. The concentration must also not be above the upper limit, because too high a concentration can be toxic or even lethal for patient P.

The control unit 2 automatically decides whether the concentration of the anesthetic in the supply gas mixture flowing through lines 31, 32 and 33 is within the target range or not. For this decision, the control unit 2 uses measured values from at least one of the two anesthetic concentration sensors 5.1 and 5.2 and/or from the volume flow sensor 5.4. As long as the measured actual concentration of the anesthetic is in the target range, the inlet 40 of the gas mixture switch 6 is connected to the regular outlet 41. The gas mixture flows from the connection line 32 into the gas mixture supply line 33 and through the gas mixture supply line 33 on to the ventilator 90. Part of this gas mixture is temporarily stored in the rear buffer storage 7.2.

If, on the other hand, the actual concentration in the mixing chamber 11, the connection line 31 and/or in the gas mixture supply line 33 is outside the setpoint range, the control unit 2 activates the gas mixture switch 6 so that the inlet 40 is now connected to the discharge outlet 42. The gas mixture from the connection line 32 therefore flows through the discharge line 35 to the gas receptacle 22 and no longer into the gas mixture supply line 33. The gas mixture with the faulty concentration is therefore kept away from the ventilator 90 and thus from the patient P. The gas receptacle 22 receives the gas flowing through the line 35 and prevents anesthetic from leaking into the environment of the anesthesia system 1, which is undesirable.

In one embodiment of the invention, the control unit 2 controls the gas mixture switch 6 depending on measured values of the rear anesthetic concentration sensor 5.2. In one possible implementation, the control unit 2 additionally uses measured values of the front anesthetic concentration sensor 5.1 and/or the volume flow sensor 5.4. If the measured values of the front anesthetic concentration sensor 5.1 and/or the volume flow sensor 5.4 indicate that the concentration of the anesthetic in the gas mixture supply line 33 will be outside the target range despite control unit 2 interventions, the control unit 2 activates the gas mixture switch 6 and causes the gas mixture to be directed from the connection line 32 to the discharge outlet 42 and to flow through the discharge line 35 to the gas receptacle 22.

The control unit 2 is also capable of controlling the bypass switch 56 downstream of the mixers—9.1, 9.2, . . . of the carrier gas mixing unit 9. This bypass switch 56 is described in more detail below.

When the gas mixture switch 6 directs the gas mixture into the discharge line 35, the ventilator 90 no longer receives any gas mixture from the anesthetic dispenser 3. The ventilator 90 is still supplied with the required gas mixture from the rear buffer storage 7.2 for a certain time. Thanks to the rear buffer storage 7.2, it is not necessary in many cases to disconnect the patient P from the anesthesia system 1 even if the gas mixture switch 6 directs the gas mixture into the discharge line 35. Such disconnection would in many cases interrupt the anesthetization of patient P and should therefore be avoided.

In an embodiment, the volume of the rear buffer storage 7.2 is variable, preferably in that at least one wall of the rear buffer storage 7.2 is elastic. In one embodiment, a hand-held respiratory bag is used as the rear buffer storage 7.2. The front buffer storage 7.1 can have a rigid housing.

In one embodiment, the respective storage capacity of the two buffer storages 7.1 and 7.2 can be configured depending on the following parameters of the supply arrangement 100:

from the volume flow of the gas mixture from the anesthetic dispenser 3 to the ventilator 90 and of the time required for the control unit 2 to detect a concentration outside the target range depending on measured values of at least one anesthetic concentration sensor 5.1, 5.2 and for the gas mixture switch 6 to be switched over in order to divert the gas mixture into the discharge line 35.

Preferably, the control unit 2 generates an alarm when the gas mixture is directed from the line 32 to the discharge line 35 and from there to the gas receptacle 22 and not to the gas mixture supply line 33 and from there to the ventilator 90. In this case, the control unit 2 and/or a user decide which of the following actions will be performed:

The incorrect actual concentration of the anesthetic has been caused by an incorrect presetting of the target concentration or by only a brief malfunction of the anesthetic dispenser 3 or the supply port 21. The actual concentration comes back into the target range in which it must be, for example by a corrected presetting or by an automatic self-correction of the anesthetic dispenser 3 or the supply port 21. As soon as the actual concentration is back in the target range, the control unit 2 preferably automatically switches the gas mixture switch 6 back to the previous state so that the gas mixture reaches the regular outlet 41 and on to the ventilator 90.

The anesthetic dispenser 3 must be switched off and restarted and then tested, in particular automatically calibrated.

The carrier gas mixing unit 9 must be switched off and restarted and then tested, in particular automatically calibrated.

The period of time during which the ventilator 90 is supplied with the gas mixture from the rear buffer storage 7.2 is usually sufficient for the anesthetic dispenser 3 to correct itself. In many cases, the time span is also sufficient for the anesthetic dispenser 3 and/or the carrier gas mixing unit 9 to be switched off, restarted and tested.

If this time period is not sufficient, the control unit 2 causes the proportional valve 8 to be opened and the bypass switch 56 to be switched. Pure oxygen or even breathing air flows from the supply port 21 through the bypass line 34 into the gas mixture supply line 33 and from there to the ventilator 90. Such a function with a bypass line 34 is described, for example, in DE 20 2011 102 318 U1 (corresponding U.S. Pat. No. 9,283,347 is hereby incorporated by reference). Possible embodiments are described below with reference to FIG. 3 and FIG. 4.

In the embodiment just described, the gas mixture is directed from line 32 to discharge line 35 and from there to gas receptacle 22 when the control unit 2 has detected a concentration of the anesthetic outside the target range. In one embodiment, the anesthetic dispenser 3 must perform a self-test from time to time, optionally with subsequent calibration, and even if no malfunction has been detected. The control unit 2 repeatedly switches the anesthetic dispenser 3 to a self-test mode after a predetermined period of use has elapsed and, in doing so, controls the gas mixture switch 6 so that the gas mixture switch 6 directs the gas mixture from the line 32 to the discharge line 35. Therefore, the self-test does not affect the concentration of an anesthetic in the gas mixture. The ventilator 90 is supplied with the required gas mixture from the rear buffer storage 7.2.

Figure 3:
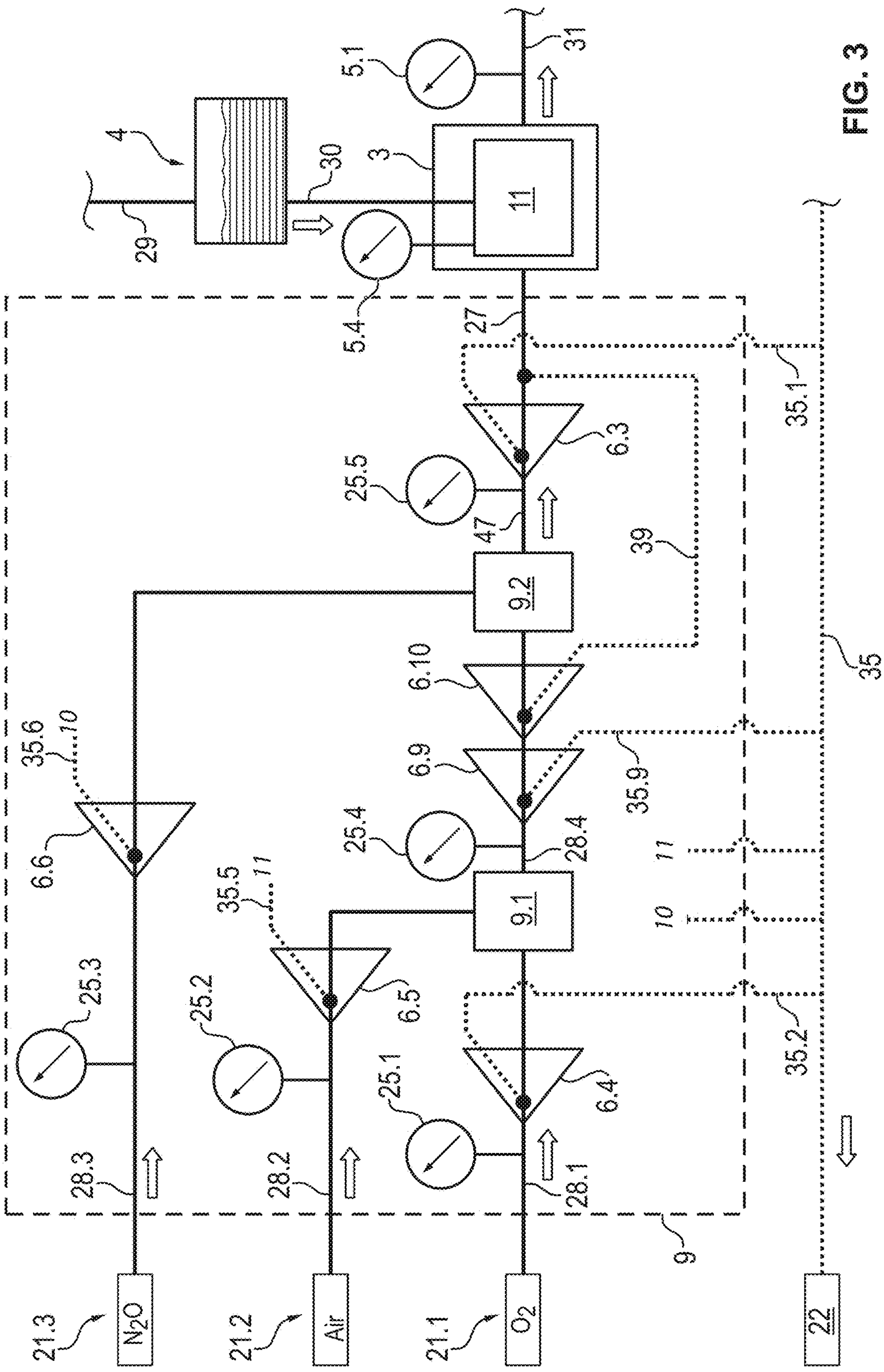
FIG. 3 is a schematic view showing a serial configuration of the carrier gas mixing unit with a feed into the discharge line.
Figure 4:
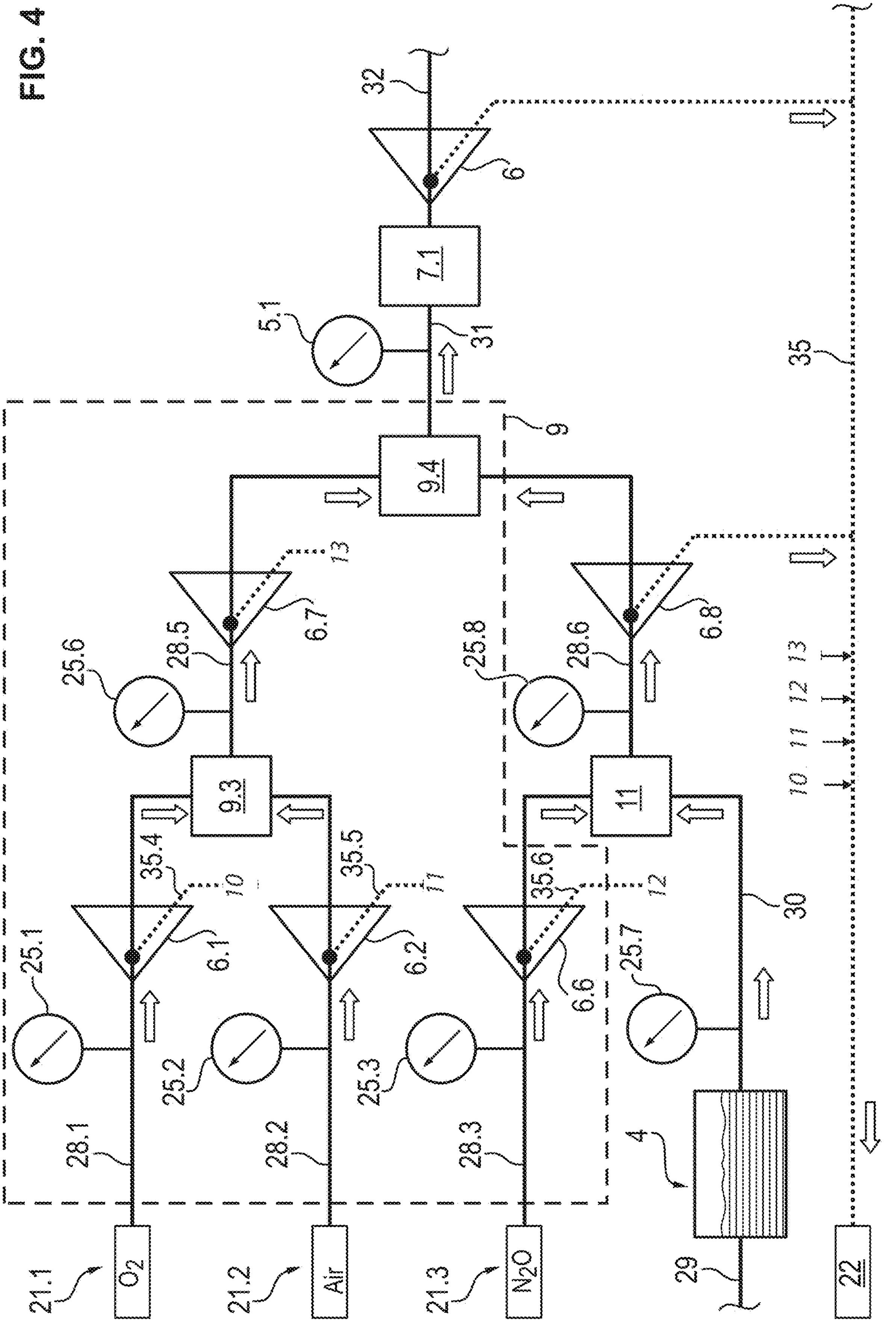
FIG. 4 is a schematic view showing a cascaded configuration of the carrier gas mixing unit with several feeds into the discharge line.

FIG. 3 and FIG. 4 show two possible embodiments of how a usable carrier gas can be produced despite a possible malfunction of a mixer 9.1, 9.2, . . . of the carrier gas mixing unit 9 or of a supply connection 21. In the example shown, the carrier gas is to be composed of the three gases oxygen, breathing air and nitrous oxide, whereby the three required proportions of the three gases in the carrier gas and a required volume flow of the carrier gas are specified. These specifications result in a required volume flow for each of the three gases breathing air, oxygen and nitrous oxide to the carrier gas mixing unit 9. One principle of the two embodiments shown is that, as far as possible, the carrier gas or the gas mixture of the carrier gas and the anesthetic is used, even if a carrier gas component is not supplied correctly.

FIG. 3 shows an embodiment in which the gas mixture is generated by supplying the three carrier gas components oxygen, breathing air and nitrous oxide (N2O) and then the anesthetic in series. Supply ports 21.1, 21.2, 21.3 feed oxygen and breathing air and nitrous oxide, respectively, into supply lines 28.1 and 28.2 and 28.3, respectively. A mixer 9.1 feeds the breathing air from supply line 28.2 into the stream of oxygen flowing through supply line 28.1. A mixture of oxygen and breathing air flows through line 28.4. A mixer 9.2 feeds nitrous oxide from supply line 28.3 into this mixture of oxygen and breathing air, producing the carrier gas. The carrier gas flows through the two carrier gas supply lines 47 and 27 to the mixing chamber 11. In the mixing chamber 11, the anesthetic is added to this carrier gas.

Three volume flow sensors 25.1, 25.2, and 25.3 each measure an indicator for the volume flow of oxygen, breathing air, and nitrous oxide, respectively, in the supply line 28.1, 28.2, and 28.3, respectively. A volume flow or concentration sensor 25.4 measures at a measurement point in the line 28.4 a measure of the volume flow of the mixture of oxygen and air and/or
the concentration of breathing air and/or
the concentration of oxygen in this mixture.

A volume flow or concentration sensor 25.5 measures, at a measurement point in the rear carrier gas supply line 27, a measure of the volume flow of the carrier gas and/or
the concentration of breathing air in the carrier gas and/or
the concentration of oxygen in the carrier gas and/or
the concentration of nitrous oxide in the carrier gas.

In one embodiment, sensors 25.4, 25.5 are also connected to the central concentration measurement unit described above.

The aforementioned anesthetic concentration sensor 5.1 measures the concentration of anesthetic in the gas mixture flowing through the connection line 31.

It is possible that the volume flow of one of the three carrier gas components oxygen, breathing air and nitrous oxide for the carrier gas is outside a specified volume flow range. A special case is that a carrier gas component is not injected at all due to a fault. It is also possible that the concentration of one of these three components in the carrier gas is outside a specified concentration range. In either case, the carrier gas that reaches the mixing chamber 11 is composed of the other two components. Even then, the carrier gas still comprises oxygen. This is shown in FIG. 3 as an example for the carrier gas component nitrous oxide, which is provided by the supply port 21.3.

The volume flow sensor 25.3 measures the volume flow of nitrous oxide through the supply line 28.3. The volume flow or concentration sensor 25.5 measures the volume flow of carrier gas through the rear carrier gas supply line 27 and/or the concentration of nitrous oxide in the carrier gas. If the volume flow and concentration of oxygen, breathing air and nitrous oxide through the supply lines 28.1, 28.2 and 28.3 respectively are correct, the mixer 9.2 feeds the nitrous oxide into the already generated mixture of oxygen and air.

If the control unit 2 detects that the volume flow or concentration of nitrous oxide through the rear carrier gas supply line 27 is too large or too small, or that no nitrous oxide is being supplied at all, the following two steps are triggered:

A carrier gas switch 6.3 directs the gas mixture with the incorrect volume flow or concentration of nitrous oxide from the rear carrier gas supply line 27 into a line 35.1. This line 35.1 opens into the discharge line 35, which in turn leads to the gas receptacle 22.

A mixer bypass switch 6.10 directs the mixture of oxygen and breathing air, which flows through line 28.4 and which has the correct volume flow, into a mixer bypass line 39. This mixer bypass line 39 opens downstream of mixer 9.2 and upstream of the carrier gas switch 6.3 into the rear carrier gas supply line 27, thus bypassing the mixer 9.2 and also the sensor 25.5. A mixture of oxygen and air then flows through the rear carrier gas supply line 27 into the mixing chamber 11.

This embodiment allows a usable carrier gas to be provided despite an incorrect volume flow or concentration of nitrous oxide, namely from the other two components of breathing air and oxygen. It is not necessary to interrupt the operation of the supply arrangement 100.

In one possible embodiment, the reaction to the detection that the volume flow or concentration of nitrous oxide is too high is as follows: The carrier gas switch 6.3 is repeatedly switched, and thereby the carrier gas switch 6.3 alternately diverts the gas mixture into the supply line 31 or into the discharge line 35. This embodiment reduces the concentration of nitrous oxide in the carrier gas, but ensures that the carrier gas contains nitrous oxide. According to this embodiment, the reaction to a too low volume flow or concentration is as follows: Carrier gas component switches 6.4 and 6.5 for oxygen and breathing air are repeatedly switched over so that the concentration of nitrous oxide is increased.

If the volume flow or concentration sensor 25.4 measures an incorrect volume flow or concentration of oxygen or breathing air in the line 28.4, the control unit 2 controls a carrier gas switch 6.9. The actuated carrier gas switch 6.9 directs the gas or gas mixture flowing through line 28.4 into a line 35.9. This line 35.9 leads into the discharge line 35. It is also possible that the control unit 2 actuates the gas mixture switch 6 in such a way that the actuated gas mixture switch 6 directs the supply gas mixture to the discharge outlet 42. Both configurations rule out with a high degree of certainty that the patient P receives a supply gas mixture with too low a proportion of oxygen.

FIG. 3 also shows a carrier gas component switch 6.5 in the supply line 28.2 for breathing air and a carrier gas component switch 6.6 in the supply line 28.3 for nitrous oxide. If the volume flow sensor 25.2 measures an incorrect or missing volume flow of breathing air through the supply line 28.2, the carrier gas component switch 6.5 diverts the flow of breathing air from the line 28.2 into a line 35.5. If the volume flow sensor 25.3 measures an incorrect or missing volume flow of nitrous oxide through the supply line 28.3, the carrier gas component switch 6.6 diverts the flow of nitrous oxide from the line 28.3 into a line 35.6. The lines 35.5 and 35.6 open into the discharge line 35.

It is possible to provide at least one bypass line for the mixer 9.1 in the same way as just described for nitrous oxide. Thanks to this bypass line for the mixer 9.1, it is possible for the carrier gas to contain breathing air but no oxygen or, conversely, oxygen but no breathing air. It is ensured that the carrier gas contains breathing air or oxygen or both. In general, it is possible to provide such a bypass line for each mixer of the supply arrangement 100.

FIG. 4 shows an example of a different configuration in which the three gases oxygen, breathing air and nitrous oxide as well as the anesthetic are supplied in cascade. Identical reference signs have the same meanings as in FIG. 3. A mixer 9.3 mixes the two components oxygen and air of the carrier gas to form an intermediate gas mixture which flows through the line 28.5. An intermediate gas mixture of nitrous oxide and gaseous anesthetic is generated in the mixing chamber 11. This intermediate gas mixture flows through line 28.6. Mixer 9.3 is arranged parallel to mixing chamber 11. Mixer 9.4 generates the desired gas mixture consisting of the carrier gas with oxygen, breathing air and nitrous oxide and the anesthetic from the two gas mixtures in the two lines 28.5 and 28.6.

In the embodiment shown in FIG. 4, six volume flow sensors are provided, namely the three volume flow sensors 25.1, 25.2, 25.3 as in the embodiment according to FIG. 3, as well as a further volume flow sensor 25.7, which measures the volume flow of liquid anesthetic in line 30. The two volume flow or concentration sensors 25.6, 25.8 measure the concentration of a component or the volume flow in the lines 28.5 and 28.6, respectively, and can also be connected to the central concentration measuring unit.

A carrier gas component switch 6.1 is able to direct oxygen, which flows through the supply line 28.1, optionally to the mixer 9.3 or into the discharge line 35. A carrier gas component switch 6.2 is capable of directing breathing air, which flows through the supply line 28.2, selectively to the mixer 9.3 or into the discharge line 35. A carrier gas component switch 6.6 is capable of directing nitrous oxide, which flows through the supply line 28.3, selectively to the mixing chamber 11 or into the discharge line 35. A carrier gas switch 6.7 is capable of directing the gas mixture of oxygen and breathing air, which flows from the mixer 9.3 through the line 28.5, selectively to the mixer 9.4 or into the discharge line 35. A carrier gas switch 6.8 is capable of directing the gas mixture of nitrous oxide and anesthetic, which flows from the mixing chamber 11 through line 28.6, either to the mixer 9.4 or into the discharge line 35.

Again, the following advantage is achieved: If one of the three components oxygen, breathing air and nitrous oxide of the carrier gas is not sufficiently provided, a carrier gas can still be provided, said carrier gas comprising breathing air and/or oxygen.

If too high a volume flow and/or too high a concentration of nitrous oxide is detected, the carrier gas component switch 6.6 is preferably repeatedly switched over and directs nitrous oxide alternately to the mixing chamber 11 or into the discharge line 35. This reduces the volume flow of nitrous oxide into the mixing chamber 11, and yet the mixing chamber 11 continues to be used. In one embodiment, if the concentration of nitrous oxide is too low, the carrier gas switch 6.7 is repeatedly switched so that the concentration of the two components oxygen and breathing air is reduced.

With reference to FIG. 2, a bypass line 34 was described above which directs a gas from the carrier gas mixing unit 9 directly to the gas mixture supply line 33 and thus into the ventilator 90. This bypass line 34 bypasses the anesthetic dispenser 3 and the two buffer storages 7.1 and 7.2. The bypass switch 56 of the carrier gas mixing unit 9 is capable of directing a component of the carrier gas into this bypass line 34.

Figure 5:
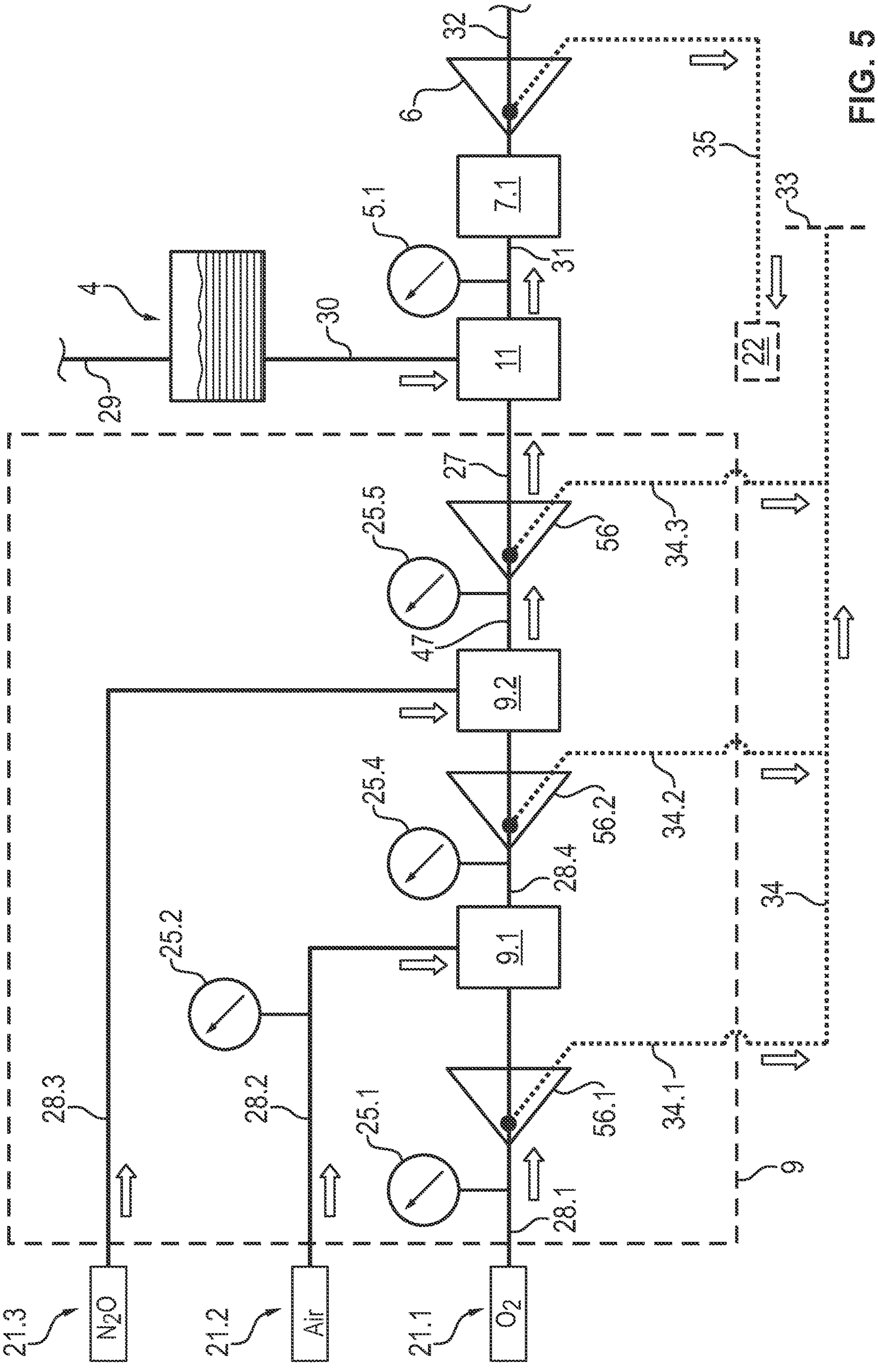
FIG. 5 is a schematic view showing a serial configuration of the carrier gas mixing unit with a feed into the bypass line.
Figure 6:
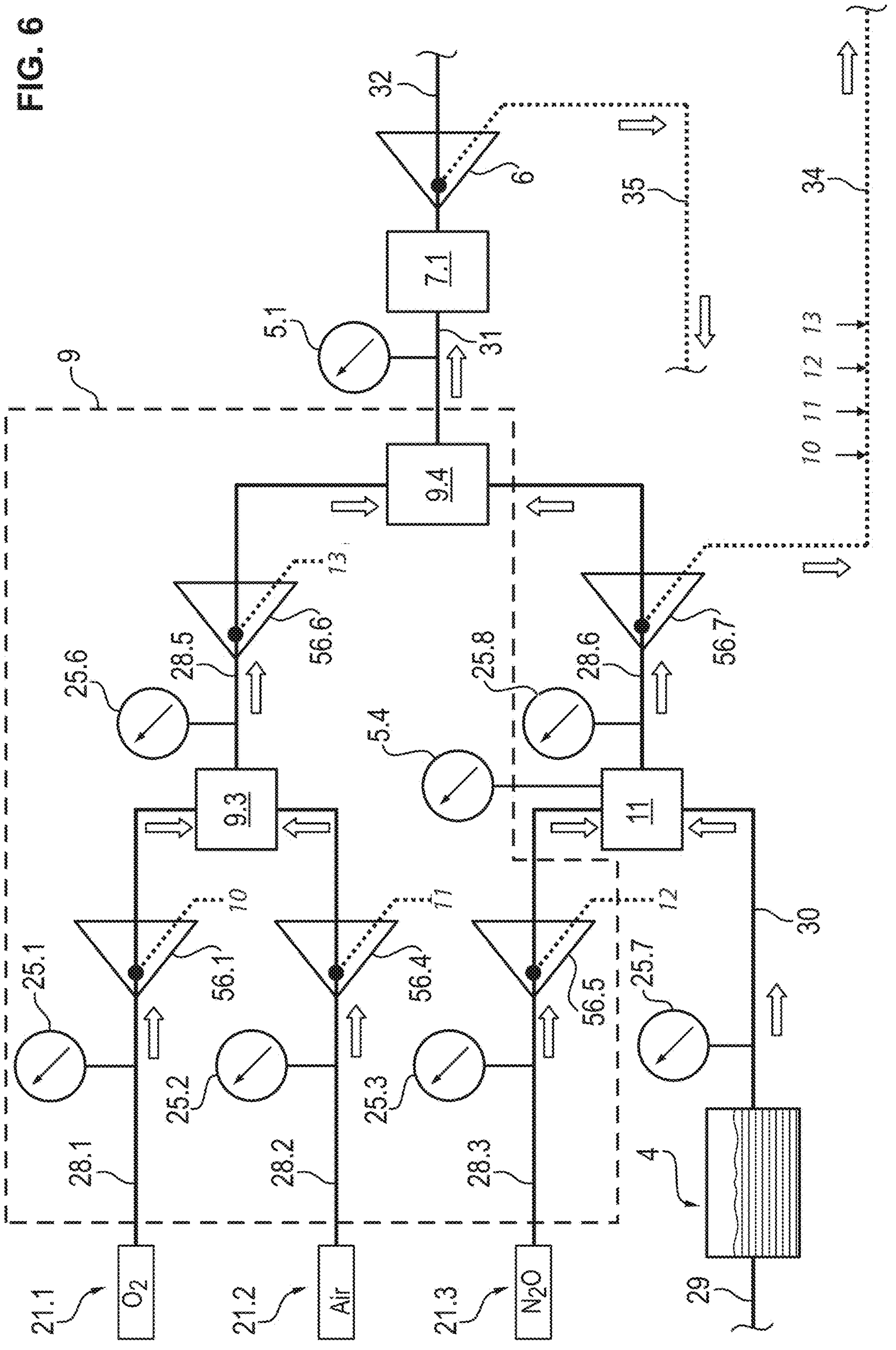
FIG. 6 is a schematic view showing a cascaded configuration of the carrier gas mixing unit with several feeds into the bypass line.

FIG. 5 and FIG. 6 show two configurations of this bypass switch 56 in the carrier gas mixing unit 9. The configuration according to FIG. 5 corresponds to the serial mixing according to FIG. 3, the configuration according to FIG. 6 corresponds to the cascaded mixing according to FIG. 4. The same reference signs again have the same meanings. The embodiments of FIG. 3 and FIG. 5 can be combined with each other, and the embodiments of FIG. 4 and FIG. 6 can also be combined with each other.

In the embodiment shown in FIG. 5, a pneumatic carrier gas component bypass switch 56.1 is capable of selectively directing oxygen flowing through the supply line 28.1 to the mixer 9.1 or into a line 34.1, wherein the line 34.1 leads to the bypass line 34. A pneumatic carrier gas component bypass switch 56.2 is capable of selectively directing the gas mixture flowing through line 28.4 to mixer 9.2 or into a line 34.2, with line 34.2 also leading to bypass line 34. The bypass switch 56 also shown in FIG. 2 is capable of selectively directing the gas mixture flowing through the front carrier gas supply line 47 into the carrier gas supply line 27 and thus to the mixing chamber 11, or into a line 34.3, the line 34.3 also leading to the bypass line 34.

This embodiment allows oxygen, breathing air, nitrous oxide, or a combination of several of these gases to be selectively introduced into the bypass line 34 and supplied to the patient P, bypassing the anesthetic dispenser 3. An exemplary possibility is explained for the following case: the volume flow or concentration sensor 25.5 has detected that the volume flow of carrier gas through the further carrier gas supply line 47 or the concentration of a component in the carrier gas is incorrect. In this case, oxygen or breathing air, or a mixture of oxygen and breathing air, is directed into the bypass line 34 from the carrier gas component bypass switches 56.1 and/or 56.2. The carrier gas in the front carrier gas supply line 47 is fed into the discharge line 35, for example from the carrier gas switch 6.3 described with reference to FIG. 3.

In the embodiment shown in FIG. 6, the carrier gas component bypass switches 56.1 and 56.4 are capable of directing oxygen or breathing air selectively to the mixer 9.3 or to the bypass line 34. The carrier gas component bypass switch 56.5 is capable of selectively conducting nitrous oxide or liquid anesthetic to the mixing chamber 11 or to the bypass line 34. The carrier gas component bypass switches 56.6 and 56.7 are capable of directing the intermediate gas mixture in lines 28.5 and 28.6, respectively, selectively to the mixer 9.4 or to the bypass line 34.

In both embodiments, the control unit 2 preferably controls the switches 56.1 to 56.7 depending on measured values of the volume flow sensors 25.1 to 25.8.

While specific embodiments of the invention have been shown and described in detail to illustrate the application of the principles of the invention, it will be understood that the invention may be embodied otherwise without departing from such principles.

| List of reference characters | |
|---|---|
| 1 | Anesthesia system, artificially ventilates and anesthetizes patient P, includes ventilator 90, supply arrangement 100, and gas mixture supply line 33 |
| 2 | signal-processing control unit, receives measured values from the concentration sensors 5.1, 5.2, 5.2, 25.1, . . . , controls the carrier gas mixing unit 9, the switches 6, 6.2 to 6.10, 56, 56.1 to 56.7 and the valve 8 |
| 3 | Anesthetic dispenser, receives a carrier gas from the carrier gas mixing unit 9 and liquid anesthetic from the anesthetic tank 4, generates the supply gas mixture from the carrier gas and the vaporized anesthetic in the mixing chamber 11, comprises the heater 10 and the mixing chamber 11 |
| 4 | Anesthetic tank, contains liquid anesthetic, is pressurized with gas through the supply line 29 |
| 5.1 | front anesthetic concentration sensor between the anesthetic dispenser 3 and the gas mixture switch 6, measures the concentration of the anesthetic in the gas mixture flowing through the connecting line 31 |
| 5.2 | rear anesthetic concentration sensor between the gas mixture switch 6 and the ventilator 90, measures the concentration of anesthetic in the gas mixture flowing through the gas mixture supply line 33 |
| 5.3 | patient-side concentration sensor, measures the concentration of the anesthetic in the supply gas mixture flowing through the line arrangement 37 to the patient-side coupling unit 50 |
| 5.4 | Volume flow sensor, measures the volume flow of anesthetic into the mixing chamber 11 |
| 6 | pneumatic gas mixture switch in the form of a switching valve, which directs the supply gas mixture from the line 32 selectively into the discharge line 34 or into the gas mixture supply line 33, comprises the inlet 40 and the outlets 41 and 42 |
| 6.1 | Carrier gas component switch, which selectively directs oxygen from the supply line 28.1 to the mixer 9.3 or to the discharge line 35 |
| 6.2 | Carrier gas component switch, which directs breathing air from the supply line 28.2 selectively to the mixer 9.3 or to the discharge line 35 |
| 6.3 | Carrier gas switch, which selectively directs the carrier gas in the rear carrier gas supply line 27 to the mixing chamber 11 or to the discharge line 35 |
| 6.4 | Carrier gas component switch, which selectively directs oxygen from the supply port 21.1 to the mixer 9.3 or to the discharge line 35 |

-continued

| List of reference characters | |
|---|---|
| 6.5 | Carrier gas component switch, which directs breathing air from supply port 21.2 selectively to mixer 9.3 or to discharge line 35 |
| 6.6 | Carrier gas component switch, which selectively directs nitrous oxide from the supply port 21.3 to the mixing chamber 11 or to the discharge line 35 |
| 6.7 | Carrier gas switch, which directs a mixture of oxygen and breathing air either to the mixer 9.4 or to the discharge line 35 |
| 6.8 | Carrier gas switch, which directs a mixture of nitrous oxide and gaseous anesthetic selectively into mixer 9.4 or to discharge line 35 |
| 6.9 | Carrier gas switch, which selectively directs a mixture of breathing air and oxygen to line 28.4 or leads the mixture into line 35.9 |
| 6.10 | Mixer bypass switch, which selectively directs a mixture of oxygen and breathing air into mixer 9.2 or into mixer bypass line 39, acts as the carrier gas component bypass switch |
| 7.1 | front buffer storage between the anesthetic dispenser 3 and the ventilator 90, located upstream of the gas mixture switch 6 and between the lines 31 and 32 |
| 7.2 | rear buffer storage between the anesthetic dispenser 3 and the ventilator 90, located downstream of the gas mixture switch 6 and the ventilator 90, has a variable volume, is in fluid communication with the gas mixture supply line 33 |
| 8 | Proportional valve in the bypass line 34 |
| 9 | Carrier gas mixing unit, generates the carrier gas from the three gases air, N2O and O2, comprises mixers 9.1 to 9.4 |
| 9.1 | Mixer that feeds into a stream of O2 breathing air |
| 9.2 | Mixer that injects nitrous oxide into a gas mixture of O2 and breathing air |
| 9.3 | Mixer that feeds into a stream of O2 breathing air |
| 9.4 | Mixer which generates the carrier gas from the gas mixture of the gas mixer 9.3 and from the gas mixture from the mixing tank 11 |
| 10 | Heater for the mixing tank 11 |
| 11 | Mixing tank of the anesthetic dispenser 3 |
| 20 | Supply connection for compressed air |
| 21 | Supply connection for the three gases breathing air, N2O and O2 |
| 21.1 | Supply connection for O2 |
| 21.2 | Supply connection for breathing air |
| 21.3 | Supply connection for nitrous oxide (N2O) |

What is claimed is:

1. A supply arrangement for supplying a medical device with a supply gas mixture comprising a carrier gas and an anesthetic, the carrier gas being comprised of two or more carrier gas components, the supply arrangement comprising:

an anesthetic dispenser configured to generate the supply gas mixture using the anesthetic and the carrier gas, the supply gas mixture comprising the anesthetic and the carrier gas;

a gas mixture switch with a gas mixture switch inlet for receiving the supply gas mixture, a gas mixture switch regular outlet and a gas mixture switch discharge outlet, the gas mixture switch being operable in a regular position, in which a fluid connection is established between the gas mixture switch inlet and the gas mixture switch regular outlet, and in a discharge position, in which a fluid connection is established between the gas mixture switch inlet and the gas mixture switch discharge outlet, wherein the gas mixture switch is configured to direct the supply gas mixture to the gas mixture switch regular outlet or to the gas mixture switch discharge outlet depending on the position of the gas mixture switch;

a carrier gas mixing unit configured to generate the carrier gas using the carrier gas components;

a carrier gas supply line which connects the carrier gas mixing unit to the anesthetic dispenser;

a first gas mixture supply line which connects the anesthetic dispenser to the inlet of the gas mixture switch;

a second gas mixture supply line which connects the regular outlet of the gas mixture switch to the medical device;

a discharge line arrangement connecting the discharge outlet of the gas mixture switch to a gas sink that is physically separate from the medical device, or leads into an environment, the discharge line arrangement comprising a common discharge line; and a carrier gas switch arrangement comprising a carrier gas switch, wherein the carrier gas switch comprises a carrier gas switch inlet; a carrier gas switch regular outlet and a carrier gas switch discharge outlet, wherein the carrier gas switch is operable in a regular position, in which a fluid connection is established between the carrier gas switch inlet and the carrier gas switch regular outlet, and in a discharge position, in which a fluid connection is established between the carrier gas switch inlet and the carrier gas switch discharge outlet, wherein the carrier gas switch regular outlet is connected to a component of the carrier gas mixing unit or to the anesthetic dispenser and the carrier gas switch discharge outlet is connected to the common discharge line, wherein the carrier gas switch is arranged such that one or more carrier gas components flow through the carrier gas switch inlet to the carrier gas switch regular outlet or to the carrier gas switch discharge outlet depending on the position of the carrier gas switch.

2. A supply arrangement according to claim 1, further comprising:

a signal processing control unit; and a state sensor arrangement comprising a state sensor which is configured to measure an indicator for a state of a component of the supply arrangement or to measure an indicator for a state of a gas or gas mixture flowing into, through, or out of the supply arrangement, wherein the control unit is configured to control the gas mixture switch depending on a signal from the state sensor such that the gas mixture switch directs the supply gas mixture to the gas mixture switch regular outlet with the signal indicating a measured state within a predetermined permissible range and directs the supply gas mixture to the gas mixture switch discharge outlet with the signal indicating a measured state outside the predetermined permissible range.

3. A supply arrangement according to claim 2, wherein:

a required concentration range of components in the supply gas mixture is specified, which range determines a desired concentration of components of the supply gas mixture;

the state sensor arrangement comprises a component concentration sensor configured to measure an indicator for an actual concentration of the component in the supply gas mixture; and the control unit is configured to control the gas mixture switch depending on a signal from the component concentration sensor such that the gas mixture switch directs the supply gas mixture to the regular outlet with a measured concentration of the component in the supply gas mixture within the required concentration range and the gas mixture switch directs the supply gas mixture to the discharge outlet with the measured concentration outside the required concentration range.

4. A supply arrangement according to claim 1, further comprising:

a signal processing control unit; and a carrier gas component concentration sensor configured to measure an indicator for an actual concentration of a carrier gas component in a gas mixture generated by the carrier gas mixing unit, wherein a required concentration range for the carrier gas component is specified which defines a required concentration of the carrier gas component in the carrier gas or in the supply gas mixture, and wherein the control unit is configured to control the gas mixture switch or control the carrier gas switch, or control both the gas mixture switch and the carrier gas switch, depending on a signal from the carrier gas component concentration sensor such that the controlled switch directs a gas or gas mixture flowing through the inlet of the switch to the regular outlet with a concentration of the carrier gas component measured by the carrier gas component concentration sensor that is within the required concentration range, and directs a gas or gas mixture flowing through the inlet of the switch to the discharge outlet with the measured carrier gas component concentration that is outside the required concentration range.

5. A supply arrangement according to claim 1, wherein:

the carrier gas is composed of a first carrier gas component, a second carrier gas component and a third carrier gas component; and the carrier gas mixing unit comprises:

a first mixer configured to generate an intermediate gas mixture using the first and second carrier gas components; and a second mixer configured to generate the carrier gas using the intermediate gas mixture and the third carrier gas component.

6. A supply arrangement according to claim 5, wherein:

the carrier gas switch is arranged such that the inlet of the carrier gas switch is connected to an outlet of the first mixer and the regular outlet of the carrier gas switch is connected to an inlet of the second mixer; and the carrier gas switch directs the intermediate gas mixture generated by the first mixer to the second mixer in the regular position and to the discharge line arrangement in the discharge position.

7. A supply arrangement according to claim 6, further comprising:

a signal processing control unit; and a carrier gas component concentration sensor for the first carrier gas component or a carrier gas component concentration sensor for the second carrier gas component or both a carrier gas component concentration sensor for the first carrier gas component and a carrier gas component concentration sensor for the second carrier gas component, wherein a required concentration range is specified for the first carrier gas component or for the second carrier gas component or for both the first carrier gas component and for the second carrier gas component, wherein the carrier gas component concentration sensor is configured to measure an indicator for the concentration of the first carrier gas component in the intermediate gas mixture or in the carrier gas or the concentration of the second carrier gas component in the intermediate gas mixture or in the carrier gas or both the concentration of the first carrier gas component in the intermediate gas mixture or in the carrier gas and the concentration of the second carrier gas component in the intermediate gas mixture or in the carrier gas, and wherein the control unit is configured to control, depending on a signal from the carrier gas component concentration sensor, the carrier gas switch which is connected to the outlet of the first mixer.

8. A supply arrangement according to claim 5, further comprising:

a mixer bypass line that bypasses the second mixer and is connected to the carrier gas supply line; and a mixer bypass switch comprising a bypass switch inlet connected to an outlet of the first mixer, a bypass switch regular outlet connected to an inlet of the second mixer, and a bypass switch bypass outlet connected to the mixer bypass line, wherein the mixer bypass switch being in a regular position directs the intermediate gas mixture to the bypass switch regular outlet and wherein the mixer bypass switch being in a bypass position directs the intermediate gas mixture to the bypass switch bypass outlet.

9. A supply arrangement according to claim 8, further comprising:

a signal processing control unit; and a carrier gas component concentration sensor configured to measure an indicator for an actual concentration of the third carrier gas component in the carrier gas or in the supply gas mixture, wherein a required concentration range is specified for the concentration of the third carrier gas component in the carrier gas or in the supply gas mixture, and wherein the control unit is configured to control the mixer bypass switch depending on a signal from the carrier gas component concentration sensor such that the mixer bypass switch directs the intermediate gas mixture to the regular outlet with the measured actual concentration of the third carrier gas component in the supply gas mixture within the required concentration range, and directs the intermediate gas mixture to the bypass outlet, with the measured actual concentration of the third carrier gas component in the supply gas mixture outside the required concentration range.

10. A supply arrangement according to claim 1, further comprising:

a carrier gas bypass line connected to the second gas mixture supply line and bypassing the anesthetic dispenser; and a carrier gas bypass switch comprising a carrier gas bypass switch inlet connected to an outlet of the carrier gas mixing unit, a carrier gas bypass switch regular outlet connected to the carrier gas supply line or to the inlet of the gas mixture switch, and a carrier gas bypass switch bypass outlet connected to the carrier gas bypass line, wherein the carrier gas bypass switch being in a regular position switch directs the carrier gas to the carrier gas bypass switch regular outlet and wherein the carrier gas bypass switch being in a bypass position directs the carrier gas to the carrier gas bypass switch bypass outlet.

11. A supply arrangement according to claim 10, further comprising:

an anesthetic concentration sensor configured to measure an indicator for an actual concentration of the anesthetic in the supply gas mixture; and a signal processing control unit, wherein a required concentration range for the concentration of the anesthetic in the supply gas mixture is specified for the anesthetic, and wherein the control unit is configured to control the carrier gas bypass switch such that the carrier gas bypass switch directs the carrier gas to the regular outlet with the actual concentration of the anesthetic within the required concentration range and directs the carrier gas to the bypass outlet with the actual concentration of the anesthetic outside the required concentration range.

12. A supply arrangement according to claim 1, further comprising a carrier gas component supply line, wherein the carrier gas switch arrangement has an inlet connected to the carrier gas component supply line.

13. A supply arrangement according to claim 12, further comprising:

a signal processing control unit; and a carrier gas component volume flow sensor configured to measure an indicator for an actual volume flow of the carrier gas component through the associated carrier gas component supply line, wherein a target volume flow range is specified for the carrier gas component associated with the carrier gas component volume flow sensor, and wherein the control unit is configured to control the carrier gas switch arrangement to direct the carrier gas component to the carrier gas switch regular outlet if the measured actual volume flow is within the specified target volume flow range and to direct the carrier gas to the carrier gas switch discharge outlet if the measured actual volume flow is outside the specified target volume flow range.

14. An anesthetic system comprising:

a patient-side coupling unit connectable to a patient; and a supply arrangement configured to provide a supply gas mixture comprising a carrier gas and anesthetic, the carrier gas being comprised of two or more carrier gas components, the supply arrangement comprising:

an anesthetic dispenser configured to generate the supply gas mixture using the anesthetic and the carrier gas, the supply gas mixture comprising the anesthetic and the carrier gas;

a gas mixture switch with a gas mixture switch inlet for receiving the supply gas mixture, a gas mixture switch regular outlet and a gas mixture switch discharge outlet, and operable in a regular position, in which a fluid connection is established between the gas mixture switch inlet and the gas mixture switch regular outlet, and in a discharge position, in which a fluid connection is established between the gas mixture switch inlet and the gas mixture switch discharge outlet, wherein the gas mixture switch is configured to direct the supply gas mixture to the gas mixture switch regular outlet or to the gas mixture switch discharge outlet depending on the position of the gas mixture switch;

a carrier gas mixing unit configured to generate the carrier gas using the carrier gas components;

a carrier gas supply line which connects the carrier gas mixing unit to the anesthetic dispenser;

a first gas mixture supply line which connects the anesthetic dispenser to the inlet of the gas mixture switch;

a second gas mixture supply line which connects the regular outlet of the gas mixture switch to a medical device;

a discharge line arrangement which connects the discharge outlet of the gas mixture switch to a gas sink that is physically separate from the medical device, or leads into an environment, the discharge line arrangement comprising a common discharge line; and a carrier gas switch arrangement comprising a carrier gas switch, wherein the carrier gas switch comprises a carrier gas switch inlet; a gas switch regular outlet and a carrier gas switch discharge outlet and is operable in a regular position, in which a fluid connection is established between the carrier gas switch inlet and the carrier gas switch regular outlet, and in a discharge position, in which a fluid connection is established between the carrier gas switch inlet and the carrier gas switch discharge outlet, wherein the carrier gas switch regular outlet is connected to a component of the carrier gas mixing unit or to the anesthetic dispenser and wherein the carrier gas switch discharge outlet is connected to the common discharge line, wherein one or more carrier gas components flow through the carrier gas switch inlet to the carrier gas switch regular outlet or to the carrier gas switch discharge outlet depending on the position of the carrier gas switch, and wherein the second gas mixture supply line connects the regular outlet of the gas mixture switch to the medical device.

15. Anesthetic system according to claim 14, the medical device comprising a ventilator, wherein the second gas mixture supply line leads from the regular outlet of the gas mixture switch to the ventilator, and wherein the ventilator is configured to deliver the supply gas mixture to the patient-side coupling unit.

16. A process of supplying a medical device with a supply gas mixture comprising a carrier gas and an anesthetic, wherein the process is performed with a supply arrangement comprising: an anesthetic dispenser; a gas mixture switch comprising a gas mixture switch inlet, a gas mixture switch regular outlet, and a gas mixture switch discharge outlet; a carrier gas mixing unit; a carrier gas supply line connecting the carrier gas mixing unit to the anesthetic dispenser; a first gas mixture supply line connecting the anesthetic dispenser to the gas mixture switch inlet; a second gas mixture supply line connecting the gas mixture switch regular outlet to the medical device; a discharge line arrangement connecting the discharge outlet of the gas mixture switch to a gas sink that is physically separate from the medical device, or leads into an environment, the discharge line arrangement comprising a common discharge line; and a carrier gas switch arrangement comprising a carrier gas switch, wherein the carrier gas switch comprises a carrier gas switch inlet; a carrier gas switch regular outlet and a carrier gas switch discharge outlet and is operable in a regular position in which a fluid connection is established between the carrier gas switch inlet and the carrier gas switch regular outlet, and in a discharge position in which a fluid connection is established between the carrier gas switch inlet and the carrier gas switch discharge outlet, wherein the carrier gas switch regular outlet is connected to a component of the carrier gas mixing unit or to the anesthetic dispenser and wherein the carrier gas switch discharge outlet is connected to the common discharge line, the process comprising the steps of:

generating the carrier gas with the carrier gas mixing unit using at least two different carrier gas components;

generating the supply gas mixture with the anesthetic dispenser using the anesthetic and the carrier gas; and with the carrier gas switch arrangement, directing a gas or a gas mixture flowing through the carrier gas switch inlet to the carrier gas switch regular outlet or to the carrier gas switch discharge outlet depending on the position of the carrier gas switch.

* * * * *